US 11,906,463 B2

(12) United States Patent
Patolsky et al.

(10) Patent No.: US 11,906,463 B2
(45) Date of Patent: Feb. 20, 2024

(54) METHODS AND SYSTEMS FOR DETECTING BIOANALYTES

(71) Applicant: Ramot at Tel-Aviv University Ltd., Tel-Aviv (IL)

(72) Inventors: Fernando Patolsky, Rehovot (IL); Vadim Krivitsky, Bney-Ayish (IL); Marina Zverzhinetsky, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 340 days.

(21) Appl. No.: 16/326,960

(22) PCT Filed: Aug. 22, 2017

(86) PCT No.: PCT/IL2017/050933
§ 371 (c)(1),
(2) Date: Feb. 21, 2019

(87) PCT Pub. No.: WO2018/037406
PCT Pub. Date: Mar. 1, 2018

(65) Prior Publication Data
US 2019/0227028 A1  Jul. 25, 2019

Related U.S. Application Data

(60) Provisional application No. 62/377,776, filed on Aug. 22, 2016.

(51) Int. Cl.
*G01N 27/414* (2006.01)
*C12Q 1/00* (2006.01)
*G01N 33/48* (2006.01)
*G01N 33/50* (2006.01)
(Continued)

(52) U.S. Cl.
CPC ....... *G01N 27/4145* (2013.01); *A61B 5/1486* (2013.01); *A61B 5/4842* (2013.01);
(Continued)

(58) Field of Classification Search
CPC .......... G01N 27/4145; G01N 27/4146; G01N 27/3275; G01N 33/50; G01N 33/5038;
(Continued)

(56) References Cited

U.S. PATENT DOCUMENTS 7,619,290 B2   11/2009  Lieber et al.
2002/0082543 A1   6/2002  Park et al.
(Continued)

FOREIGN PATENT DOCUMENTS

CN     106164286     11/2016
KR     2011-0124855  11/2011
(Continued)

OTHER PUBLICATIONS

Joshi, Pratixa P., et al. "Amperometric biosensors based on redox polymer-carbon nanotube-enzyme composites." Analytical Chemistry 77.10 (2005): 3183-3188. (Year: 2005).*

(Continued)

*Primary Examiner* — Robert J Eom

(57) ABSTRACT

A sensing system and a method utilizing same for determining and/or monitoring a presence and/or level of an analyte in a sample are provided. The sensing system is made of a nanostructure, or a plurality of nanostructures, having covalently attached thereto and a hydrogel having associated therewith a sensing moiety which selectively interacts with the analyte and being configured such that upon contacting the analyte, the nanostructure(s) exhibit a detectable change in an electrical property.

26 Claims, 7 Drawing Sheets
(4 of 7 Drawing Sheet(s) Filed in Color)

(51) Int. Cl.
| | |
|---|---|
| *G01N 33/543* | (2006.01) |
| *G01N 33/574* | (2006.01) |
| *H10K 10/46* | (2023.01) |
| *H10K 85/60* | (2023.01) |
| *G01N 27/327* | (2006.01) |
| *C12M 1/34* | (2006.01) |
| *A61B 5/1486* | (2006.01) |
| *A61B 5/00* | (2006.01) |
| *H10K 85/00* | (2023.01) |
| *B82Y 15/00* | (2011.01) |

(52) U.S. Cl.
CPC ............... *C12M 1/34* (2013.01); *C12Q 1/00* (2013.01); *G01N 27/4146* (2013.01); *G01N 33/48* (2013.01); *G01N 33/50* (2013.01); *G01N 33/5038* (2013.01); *G01N 33/54346* (2013.01); *G01N 33/57484* (2013.01); *A61B 2562/0285* (2013.01); *A61B 2562/164* (2013.01); *A61B 2562/227* (2013.01); *B82Y 15/00* (2013.01); *G01N 27/3275* (2013.01); *H10K 10/484* (2023.02); *H10K 85/60* (2023.02); *H10K 85/761* (2023.02)

(58) Field of Classification Search
CPC ........ G01N 33/54346; G01N 33/57484; A61B 5/1486; A61B 5/4842; A61B 2562/0285; A61B 2562/164; A61B 2562/227; C12M 1/34; C12Q 1/00; B82Y 15/00; H01L 51/0093; H01L 51/0558
See application file for complete search history.

(56) References Cited

U.S. PATENT DOCUMENTS

| | | | |
|---|---|---|---|
| 2002/0117659 A1* | 8/2002 | Lieber | H01L 23/53276 257/E29.081 |
| 2002/0133129 A1 | 9/2002 | Arias et al. | |
| 2003/0153900 A1 | 8/2003 | Aceti et al. | |
| 2003/0190632 A1 | 10/2003 | Sosnlwski et al. | |
| 2007/0111196 A1 | 5/2007 | Alarcon et al. | |
| 2009/0170209 A1 | 7/2009 | Machauf et al. | |
| 2010/0022012 A1 | 1/2010 | Lieber et al. | |
| 2010/0152057 A1 | 6/2010 | Lieber et al. | |
| 2010/0325073 A1 | 12/2010 | Haick | |
| 2012/0134880 A1 | 5/2012 | Kurkina et al. | |
| 2012/0172692 A1 | 7/2012 | Tamada et al. | |
| 2012/0187000 A1 | 7/2012 | Kahn et al. | |
| 2012/0265034 A1 | 10/2012 | Wisniewski et al. | |
| 2014/0286875 A1 | 9/2014 | Gamsey et al. | |
| 2014/0336487 A1 | 11/2014 | Wang et al. | |
| 2015/0231633 A1 | 8/2015 | Dubin et al. | |
| 2015/0307936 A1 | 10/2015 | Goldsmith | |
| 2015/0376692 A1 | 12/2015 | Esfandyarpour et al. | |
| 2016/0095541 A1 | 4/2016 | Wang et al. | |
| 2019/0223795 A1 | 7/2019 | Patolsky et al. | |

FOREIGN PATENT DOCUMENTS

| | | |
|---|---|---|
| KR | 101359349 | 1/2014 |
| WO | WO 2010/099446 | 9/2010 |
| WO | WO 2011/000443 | 1/2011 |
| WO | WO 2012/137207 | 10/2012 |
| WO | WO 2015/059704 | 4/2015 |
| WO | WO 2015/192064 | 12/2015 |
| WO | WO 2016/032335 | 3/2016 |
| WO | WO 2018/037406 | 3/2018 |
| WO | WO 2018/037407 | 3/2018 |

OTHER PUBLICATIONS

Biondi, Marco, et al. "Nanoparticle-integrated hydrogels as multifunctional composite materials for biomedical applications." Gels 1.2 (2015): 162-178. (Year: 2015).*

Sharma, Piyush Sindhu, Francis D'Souza, and Wlodzimierz Kutner. "Graphene and graphene oxide materials for chemo-and biosensing of chemical and biochemical hazards." Making and Exploiting Fullerenes, Graphene, and Carbon Nanotubes (2013): 237-265. (Year: 2013).*

Lee, Sung W., et al. "Periodic array of polyelectrolyte-gated organic transistors from electrospun poly (3-hexylthiophene) nanofibers." Nano letters 10.1 (2010): 347-351. (Year: 2010).*

Cao, Anping, et al. "Ionophore-containing siloprene membranes: direct comparison between conventional ion-selective electrodes and silicon nanowire-based field-effect transistors." Analytical chemistry 87.2 (2014): 1173-1179. (Year: 2014).*

Reinhoudt, David N., and Ernst Jr Sudhölter. "The transduction of host-guest interactions into electronic signals by molecular systems." Advanced materials 2.1 (1990): 23-32. (Year: 1990).*

Munoz, J., et al. "Photosensitive polyurethanes applied to the development of CHEMFET and ENFET devices for biomedical sensing." Biosensors and Bioelectronics 12.7 (1997): 577-585. (Year: 1997).*

Buenger, Daniel, Fuat Topuz, and Juergen Groll. "Hydrogels in sensing applications." Progress in Polymer Science 37.12 (2012): 1678-1719. (Year: 2012).*

Supplementary European Search Report and the European Search Opinion dated Feb. 10, 2020 From the European Patent Office Re. Application No. 17843059.1. (8 Pages).

Katz et al. "Glucose Oxidase Electrodes Via Reconstitution of the Apo-Enzyme: Cailoring of Novel Glucose Biosensors", Analytica Chimica Acta, XP8043785, 385,(1-3): 45-58, Apr. 5, 1999.

Official Action dated Mar. 2, 2021 From the US Patent and Trademark Office Re. U.S. Appl. No. 16/326,385. (24 Pages).

Supplementary European Search Report and the European Search Opinion dated Feb. 27, 2020 From the European Patent Office Re. Application No. 17843058.3. (7 Pages).

International Preliminary Report on Patentability dated Mar. 7, 2019 From the International Bureau of WIPO Re. Application No. PCT/IL2017/050933. (7 Pages).

International Preliminary Report on Patentability dated Mar. 7, 2019 From the International Bureau of WIPO Re. Application No. PCT/IL2017/050935. (7 Pages).

International Search Report and the Written Opinion dated Dec. 4, 2017 From the International Searching Authority Re. Application No. PCT/IL2017/050933. (25 Pages).

International Search Report and the Written Opinion dated Dec. 10, 2017 From the International Searching Authority Re. Application No. PCT/IL2017/050935. (12 Pages).

Chen et al. "Silicon Nanowire Field-Effect Transistor-Based Biosensors for Biomedical Diagnosis and Cellular Recording Investigation", Nano Today, 6(2): 131-154, Available Online Mar. 8, 2011.

Clavaguera et al. "Sub-PPM Detection of Nerve Agents Using Chemically Functionalized Silicon Nanoribbon Field-Effect Transistors", Angewandte Chemie International Edition, 49(24): 4063-4066, Jun. 1, 2010.

Cui et al. "Nanowire Nanosensors for Highly Sensitive and Selective Detection of Biological and Chemical Species", Science, 293(5533): 1289-1292, Aug. 17, 2001.

Duan et al. "Intracellular Recordings of Action Potentials by An Extracellular Nanoscale Field-Effect Transistor", Nature Nanotechnology, 7(3): 174-179, Published Online Dec. 18, 2011.

Griffin et al. "Metabolic Profiles of Cancer Cells", Nature Reviews Cancer, 4(7): 551-561, Jul. 2004.

Han et al. "Mutiscale Substrates Based on Hydrogel-Incorporated Silicon Nanowires for Protein Patterning and Microarray-Based Immunoassays", Biosensors and Bioelectronics, 45: 129-135, Available Online Feb. 6, 2013.

Kosaka et al. "Detection of Cancer Biomarkers in Serum Using A Hybrid Mechanical and Optoplasmonic Nanosensor", Nature Nanotechnology, 9(12): 1047-1053, Published Online Nov. 2, 2014.

Krivitsky et al. "Si Nanowires Forest-Based On-Chip Biomolecular Filtering, Separation and Preconcentration Devices: Nanowires Do It All", Nano Letters, 12(9): 4748-4756, Published Online Aug. 2, 2012.

(56) References Cited

OTHER PUBLICATIONS

Li et al. "Sequence-Specific Label-Free DNA Sensors Based on Silicon Nanowires", Nano Letters, 4(2): 245-247, Feb. 11, 2004.
Lu et al. "A Nano-Ni Based Ultrasensitive Nonenzymatic Electrochemical Sensor for Glucose: Enhancing Sensitivity Through A Nanowire Array Strategy", Biosensors and Bioelectronics, 25(1): 218-223, Published Online Jul. 7, 2009.
Lu et al. "Enzyme-Functionalized Gold Nanowires for the Fabrication of Biosensors", Bioelectrochemistry, 71(2): 211-216, Published Online Jun. 14, 2007.
Munoz-Pinedo et al. "Cancer Metabolism: Current Perspectives and Future Directions", Cell Death and Disease, 3(1): e248-1-e248-10, Jan. 12, 2012.
Patolsky et al. "Electrical Detection of Single Viruses", Proc. Natl. Acad. Sci. USA, PNAS, 101(39): 14017-14022, Sep. 28, 2004.
Patolsky et al. "Nanowire-Based Biosensors", Analytical Chemistry, 78(13): 4260-4269, Jul. 1, 2006.
Piao et al. "Enzyme Incorporated Microfluidic Device for In-Situ Glucose Detection in Water-in-Air Microdroplets", Biosensors and Bioelectronics, 65: 220-225, Available Online Oct. 18, 2014.
Revzin et al. "Fabrication of Poly(Ethylene Glycol) Hydrogel Microstructures Using Photolithography", Langmuir, 17(18): 5440-5447, Published Jul. 18, 2001.
Shao et al. "Silicon Nanowire Sensors for Bioanalytical Applications: Glucose and Hydrogen Peroxide Detection", Advanced Functional Materials, 15(9): 1478-1482, Sep. 1, 2005.
Stern et al. "Label-Free Biomarker Detection From Whole Blood", Nature Nanotechnology, 5(2): 138-142, Published Online Dec. 13, 2009.
Stern et al. "Semiconducting Nanowire Field-Effect Transistor Biomolecular Sensors", IEEE Transactions on Electron Devices, 55(11): 3119-3130, Nov. 2008.
Su et al. "A Silicon Nanowire-Based Electrochemical Sensor With High Sensitivity and Electrocatalytic Activity", Particle Particle Systems Characterization, 30(4): 326-331, Apr. 1, 2013.
Timko et al. "Electrical Recording From Hearts With Flexible Nanowire Device Arrays", Nano Letters, 9(2): 914-918, Feb. 2009.
Tyagi et al. "Patternable Nanowire Sensors for Electrochemical Recording of Dopamine", Analytical Chemistry, 81(24): 9979-9984, Dec. 15, 2009.
Yang et al. "Gold Nanoparticle Modified Silicon Nanowires as Biosensors", Nanotechnology, 17(11): S276-S279, May 19, 2006.
Zheng et al. "Multiplexed Electrical Detection of Cancer Markers With Nanowire Sensor Arrays", Nature Biotechnology, 23(10): 1294-1301, Oct. 2005.
Notification of Office Action and Search Report dated Aug. 10, 2021 From the State Intellectual Property Office of the People's Republic of China Re. Application No. 10780064812.4. (.
Official Action dated Jan. 14, 2022 from US Patent and Trademark Office Re. U.S. Appl. No. 16/326,385. (17 pages).
Final Official Action dated Jul. 18, 2022 from US Patent and Trademark Office Re. U.S. Appl. No. 16/326,385. (18 pages).
Official Action dated Sep. 8, 2023 from the US Patent and Trademark Office Re. U.S. Appl. No. 16/326,385. (17 pages).
Final Official Action dated Mar. 22, 2023 from the US Patent and Trademark Office Re. U.S. Appl. No. 16/326,385. (23 pages).

* cited by examiner

METHODS AND SYSTEMS FOR DETECTING BIOANALYTES

RELATED APPLICATION

PCT Patent Application No. PCT/IL2017/050933was co-filed on Aug. 22, 2017 with PCT Patent Application No. PCT/IL2017/050935, titled "METHODS AND SYSTEMS FOR SUBCUTANEOUS SENSING", which claims the benefit of priority of U.S. Provisional Patent Application No. 62/377,775 filed on Aug. 22, 2016, the contents of which are incorporated herein by reference in their entirety.

This application is a National Phase of PCT Patent Application No. PCT/IL2017/050933 having International filing date of Aug. 22, 2017, which claims the benefit of priority of U.S. Provisional Patent Application No. 62/377,776 filed on Aug. 22, 2016. The contents of the above identified applications are all incorporated herein by reference in their entirety.

FIELD AND BACKGROUND OF THE INVENTION

The present invention, in some embodiments thereof, relates to sensing and, more particularly, but not exclusively, to methods and systems for determining a presence and/or amount of analytes such as, but not limited to, bioanalytes, in a sample such as a biological sample, and to uses thereof.

The development of efficient bio-molecular separation and purification techniques is of high importance in modern genomics, proteomics, and bio-sensing areas, primarily due to the fact that most bio-samples are mixtures of high diversity and complexity. Most of the currently-practiced techniques lack the capability to rapidly and selectively separate and concentrate specific target molecules (e.g., metabolites, proteins) from a complex bio-sample, and are difficult to integrate with lab-on-a-chip sensing devices.

Detecting target metabolites represents one of the most attracting techniques, and has been extensively thought for. The development of efficient continuous metabolic sensor has critical importance in modern medicine and bio-sample analysis (in vivo and ex vivo).

Metabolism encompasses biochemical processes in living organisms that either produce or consume energy. Metabolic reactions regulate cells to grow or die, reform their structures, and respond to their environments.

Abnormal metabolic reactions disturb normal physiology and lead to severe tissue dysfunction, and are linked to many diseases, including, for example, cancer and diabetes.

Cancer is an example of a common human disease with metabolic perturbations. Altered cellular metabolism is a hallmark of cancer, contributing to malignant transformation and to the initiation, growth, and maintenance of tumors. Thus, for example, studies have shown that altered glucose metabolism promotes cancer development, and that cancer cells consume much more glucose and secrete much more lactate than normal tissue.

Understanding the complex networks associated with cancer metabolism for monitoring thereof have therefore been recognized as desirable for distinguishing metabolic significances of cancers, estimating the effectiveness of therapies, and facilitating personalized treatments. See, for example, Munoz-Pinedo et al. Cell Death Dis 2012, 3: e248; and Griffin and Shockcor, Nature reviews Cancer 2004, 4(7): 551-561.

Semiconducting nanowires are known to be extremely sensitive to chemical species adsorbed on their surfaces. For a nanowire device, the binding of a charged analyte to the surface of the nanowire leads to a conductance change, or a change in current flowing through the wires. The 1D (one dimensional) nanoscale morphology and the extremely high surface-to-volume ratio make this conductance change to be much greater for nanowire-based sensors versus planar FETs (field-effect transistors), increasing the sensitivity to a point that single molecule detection is possible.

Nanowire-based field-effect transistors (NW-FETs) have therefore been recognized in the past decade as powerful potential new sensors for the detection of chemical and biological species. See, for example, Patolsky et al., Analytical Chemistry 78, 4260-4269 (2006); Stern et al., IEEE Transactions on Electron Devices 55, 3119-3130 (2008); Cui et al., Science 293, 1289-1292 (2001); Patolsky et al. Proceedings of the National Academy of Sciences of the United States of America 101, 14017-14022 (2004), all being incorporated by reference as if fully set forth herein.

Studies have also been conducted with nanowire electrical devices for the simultaneous multiplexed detection of multiple biomolecular species of medical diagnostic relevance, such as DNA and proteins [Zheng et al., Nature Biotechnology 23, 1294-1301 (2005); Timko et al., Nano Lett. 9, 914-918 (2009); Li et al., Nano Lett. 4, 245-247 (2004)].

Generally, in a NW-FET configuration, the gate potential controls the channel conductance for a given source drain voltage (VSD), and modulation of the gate voltage (VGD) changes the measured source-drain current (ISD). For NW sensors operated as FETs, the sensing mechanism is the field-gating effect of charged molecules on the carrier conduction inside the NW. Compared to devices made of micro-sized materials or bulk materials, the enhanced sensitivity of nanodevices is closely related to the reduced dimensions and larger surface/volume ratio. Since most of the biological analyte molecules have intrinsic charges, binding on the nanowire surface can serve as a molecular gate on the semiconducting SiNW [Cui et al., 2001, supra].

Antibody/enzyme nanowire FET devices which target metabolites via binding affinity have been disclosed in, for example, Lu et al. *Bioelectrochemistry* 2007, 71(2): 211-216; Patolsky et al. Nanowire-based biosensors. *Anal Chem* 2006, 78(13): 4260-4269; and Yang et al. *Nanotechnology* 2006, 17(11): S276-S279.

Electrochemically-sensitive nanowire sensors for detecting metabolites by oxidative reactions have been disclosed in, for example, Lu et al. Biosens Bioelectron 2009, 25(1): 218-223; Shao et al. Adv Funct Mater 2005, 15(9): 1478-1482; Su et al. Part Part Syst Char 2013, 30(4): 326-331; and Tyagi et al. Anal Chem 2009, 81(24): 9979-9984.

U.S. Pat. No. 7,619,290, U.S. Patent Application having publication No. 2010/0022012, and corresponding applications, teach nanoscale devices composed of, inter alia, functionalized nanowires, which can be used as sensors.

Clavaguera et al. disclosed a method for sub-ppm detection of nerve agents using chemically functionalized silicon nanoribbon field-effect transistors [Clavaguera et al., Angew. Chem. Int. Ed. 2010, 49, 1-5].

$SiO_2$ surface chemistries were used to construct a 'nanoelectronic nose' library, which can distinguish acetone and hexane vapors via distributed responses [Nature Materials Vol. 6, 2007, pp. 379-384].

U.S. Patent Application having Publication No. 2010/0325073 discloses nanodevices designed for absorbing gaseous NO. WO 2011/000443 describes nanodevices which utilize functionalized nanowires for detecting nitro-containing compounds.

Duan et al. [Nature Nanotechnology, Vol. 7, 2012, pp. 174-179] describes a silicon nanowire FET detector and an electrically insulating $SiO_2$ nanotube that connects the FET to the intracellular fluid (the cytosol). When there is a change in transmembrane potential Vm, the varying potential of the cytosol inside the nanotube gives rise to a change in the conductance G of the FET.

Kosaka et al. [Nature Nanotechnology, Vol. 9, 2014, pp. 1047-1053] discloses detection of cancer biomarkers in serum using surface-anchored antibody.

Krivitsky et al. [Nano letters 2012, 12(9): 4748-4756] describe an on-chip all-SiNW filtering, selective separation, desalting, and preconcentration platform for the direct analysis of whole blood and other complex biosamples. The separation of required protein analytes from raw biosamples is first performed using an antibody-modified roughness-controlled SiNWs forest of ultralarge binding surface area, followed by the release of target proteins in a controlled liquid media, and their subsequent detection by SiNW-based FETs arrays fabricated on the same chip platform.

WO 2015/059704 discloses an integrated microfluidic nanostructure sensing system, comprised of one or more sensing compartments featuring a redox-reactive nanostructure FET array which is in fluid communication with one or more sample chambers. This system has been shown to perform multiplex real-time monitoring of cellular metabolic activity in physiological solutions, and was demonstrated as an efficient tool in promoting the understanding of metabolic networks and requirements of cancers for personalized medicine.

Revzin et al. Langmuir 2001, 17, 5440-5447, describe cross-linked hydrogel microstructures based upon poly(ethylene glycol) diacrylates, dimethacrylates, and tetraacrylates patterned photolithographically on silicon or glass substrates, and further describe arrays of such hydrogel disks containing an immobilized protein conjugated to a pH sensitive fluorophore.

Piao et al., Biosensors and Bioelectronics 65 (2015) 220-225, describe droplet generating microfluidic systems which can serve as a sensitive and in-situ glucose monitoring system using water-in-air droplets in an enzyme incorporated micro-fluidic device. The system is made of a thin film structure of a glucose oxidase (GOx) enzyme immobilized hydrogel constructed in the middle of the microfluidic channel, and nanoliter scaled water-in-air droplets which contain a glucose sample, horseradish peroxidase (HRP), and an Amplex Red substrate, generated by flow focusing of water phase with air. While the droplets pass through the enzyme trapped hydrogel, a GOx mediated catalytic reaction with glucose occurs, and fluorescent resorufin products are formed in the droplets.

Additional background art includes, for example, Chen et al., Nano Today (2011) 6, 131-54, and references cited therein; and Stern et al., Nature Nanotechnology, 2009.

SUMMARY OF THE INVENTION

According to an aspect of some embodiments of the present invention there is provided a sensing system for determining and/or monitoring a presence and/or level of an analyte in a sample, the system comprising a nanostructure and a hydrogel covalently attached to the nanostructure, the hydrogel having associated therewith a sensing moiety which selectively interacts with the analyte and being configured such that upon contacting the analyte, the nanostructure exhibits a detectable change in an electrical property.

According to some of any of the embodiments described herein, the sample is a biological sample.

According to some of any of the embodiments described herein, the detecting and/or monitoring is/are performed in vitro, ex vivo or in vivo.

According to some of any of the embodiments described herein, the analyte is a bioanalyte.

According to some of any of the embodiments described herein, the sensing moiety is an analyte-specific reagent.

According to some of any of the embodiments described herein, the analyte is a metabolite.

According to some of any of the embodiments described herein, the sensing moiety is a redox enzyme specific to the metabolite.

According to some of any of the embodiments described herein, the sensing moiety is an oxidase.

According to some of any of the embodiments described herein, the analyte is a biomarker protein.

According to some of any of the embodiments described herein, the analyte is an antigen and the sensing moiety is an antibody specific to the antigen.

According to some of any of the embodiments described herein, an interaction of the sensing moiety with the analyte is reversible.

According to some of any of the embodiments described herein, the hydrogel comprises a cross-linked polymeric network comprising at least one poly(alkylene glycol) polymeric chain.

According to some of any of the embodiments described herein, the hydrogel is covalently attached to the nanostructure via a linking moiety.

According to some of any of the embodiments described herein, the linking moiety comprises a hydrocarbon chain.

According to some of any of the embodiments described herein, the hydrogel is selected capable of impregnating a biological moiety while maintaining an activity of the biological moiety.

According to some of any of the embodiments described herein, upon contacting the analyte, the hydrogel exhibits a deformation, the deformation leading to the detectable change in the electrical property of the nanostructure.

According to some of any of the embodiments described herein, the deformation comprises a change in a volume of the hydrogel.

According to some of any of the embodiments described herein, the deformation comprises a change in spatial distribution of molecules and/or charge in the hydrogel.

According to some of any of the embodiments described herein, the electrical property comprises electron density on a surface of the nanostructure.

According to some of any of the embodiments described herein, the nanostructure is a nanowire.

According to some of any of the embodiments described herein, the nanostructure is a semiconductor nanostructure.

According to some of any of the embodiments described herein, the semiconductor nanostructure comprises silicon.

According to some of any of the embodiments described herein, the nanostructure is a transistor.

According to some of any of the embodiments described herein, the sensing system comprises a plurality of the nanostructures.

According to some of any of the embodiments described herein, the hydrogel is covalently attached to at least two of the nanostructures.

According to some of any of the embodiments described herein, the nanostructures are substantially identical.

According to some of any of the embodiments described herein, in at least one portion of the nanostructures the hydrogel is associated with a first sensing moiety and in at least another portion of the nanostructures the hydrogel is associated with a second sensing moiety, the first and second sensing moieties being different from one another.

According to some of any of the embodiments described herein, the sensing system further comprises at least one nanostructure having a hydrogel covalently attached thereto, the hydrogel having associated therewith a non-sensing moiety.

According to some of any of the embodiments described herein, the hydrogel is in a form of a nanoparticle.

According to some of any of the embodiments described herein, the hydrogel is a form of a film.

According to some of any of the embodiments described herein, the sensing system further comprises a substrate onto and/or into which the nanostructure is, or the plurality of nanostructures are, deposited.

According to some of any of the embodiments described herein, the sensing system is devoid of a labeling agent.

According to some of any of the embodiments described herein, the sensing system further comprises a detector constructed and arranged to determine the change in electrical property.

According to an aspect of some embodiments of the present invention there is provided a system comprising a sensing compartment comprising the sensing system as described herein in any of the respective embodiments and any combination thereof, and at least one additional compartment being in communication with the sensing compartment.

According to some of any of the embodiments described herein, the at least one additional compartment is in fluid communication with the sensing compartment.

According to some of any of the embodiments described herein, the fluid communication is effected by means of microchannels.

According to some of any of the embodiments described herein, the at least one additional compartment is configured to contain at least a portion of the sample.

According to some of any of the embodiments described herein, the at least one additional compartment is configured to contain a therapeutically active agent.

According to some of any of the embodiments described herein, the additional compartment is configured to controllably release the therapeutically active agent.

According to some of any of the embodiments described herein, the additional compartment is configured to controllably release the therapeutically active agent responsively to the detectable change in electrical property of the nanostructure.

According to some of any of the embodiments described herein, the at least one additional compartment comprises an additional sensing system.

According to some of any of the embodiments described herein, the sensing system of the system as described herein in any of the respective embodiments and any combination thereof, is configured for detecting and/or monitoring the analyte in vivo.

According to some of any of the embodiments described herein, the sensing system of the system as described herein in any of the respective embodiments and any combination thereof, is in a form a skin patch.

According to some of any of the embodiments described herein, the sensing system of the system as described herein in any of the respective embodiments and any combination thereof, is configured for detecting and/or monitoring the analyte ex vivo.

According to an aspect of some embodiments of the present invention there is provided a method of determining or monitoring a presence and/or a level of at least one analyte in a sample, the method comprising contacting at least a portion of the sample with the sensing system or the system comprising same, as described herein in any of the respective embodiments and any combination thereof, wherein the detectable change in the electrical property is indicative of the presence and/or level of the analyte in the sample.

According to some of any of the embodiments described herein, the sample is a biological sample.

According to some of any of the embodiments described herein, the biological sample is drawn from a subject, and wherein the determining and/or monitoring is effected ex-vivo.

According to some of any of the embodiments described herein, the biological sample is an organ or tissue of a subject and wherein the determining and/or monitoring is effected in vivo.

According to some of any of the embodiments described herein, the contacting is continuous.

According to some of any of the embodiments described herein, the method is for diagnosing and/or monitoring a disease associated with the analyte in a subject.

According to some of any of the embodiments described herein, the system further comprises a compartment configured for releasing a therapeutically active agent, the method being for determining and/or monitoring an efficacy of the therapeutic agent towards the disease in the subject and/or for treating the disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data.

Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D present schematic illustrations of exemplary sensing systems according to some embodiments of the present invention.

Figure 2A:
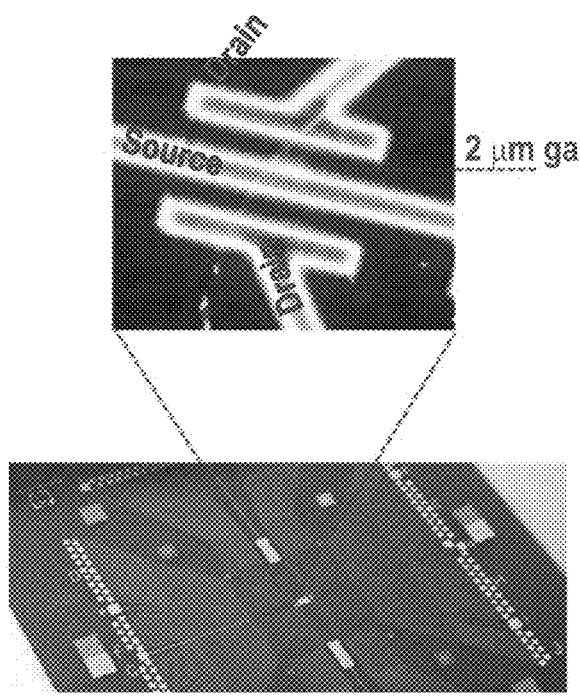
Figure 2B:
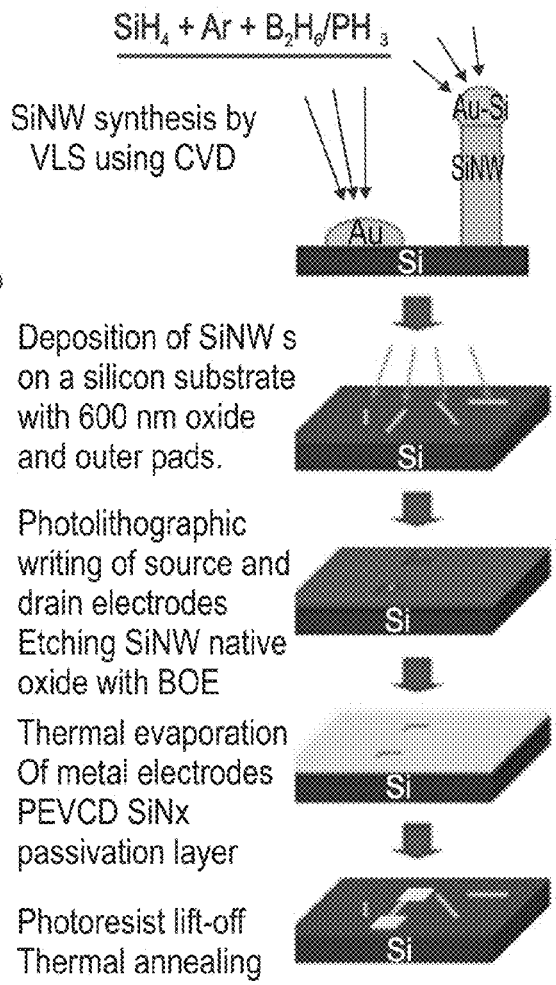

FIGS. 2A-B present schematic illustrations of a SiNW FET system used in experiments performed according to some embodiments of the present invention (FIG. 2A) and of an exemplary process of constructing the SiNW FET system (FIG. 2B).

Figure 3:
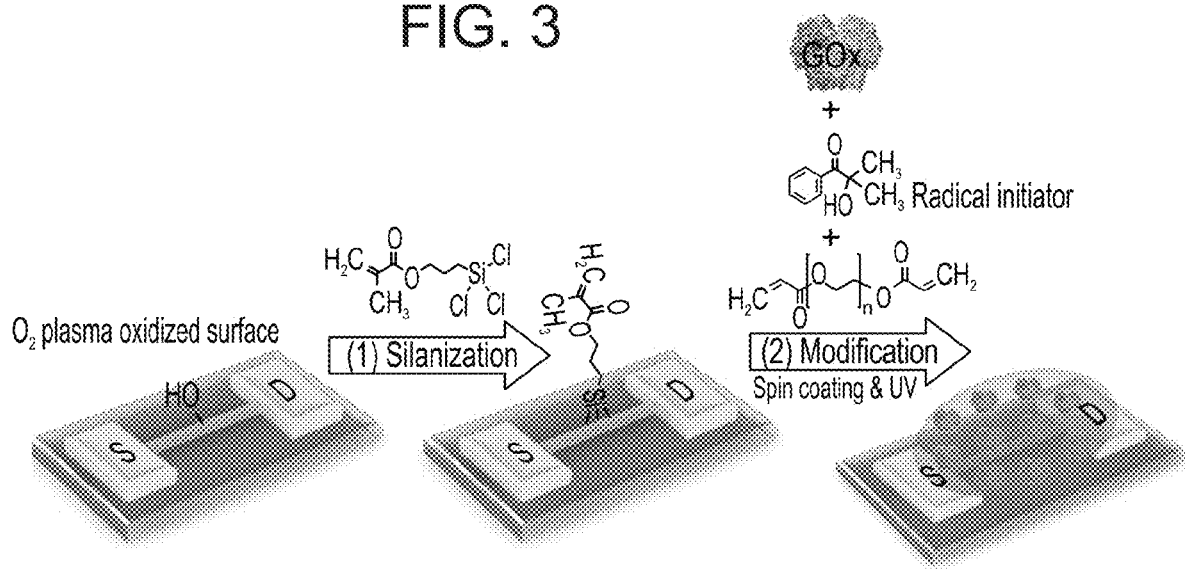

FIG. 3 is a schematic illustration of a preparation of SiNW FET system having GOx-impregnated hydrogel immobilized thereto, used in experiments performed according to some embodiments of the present invention.

Figure 4:
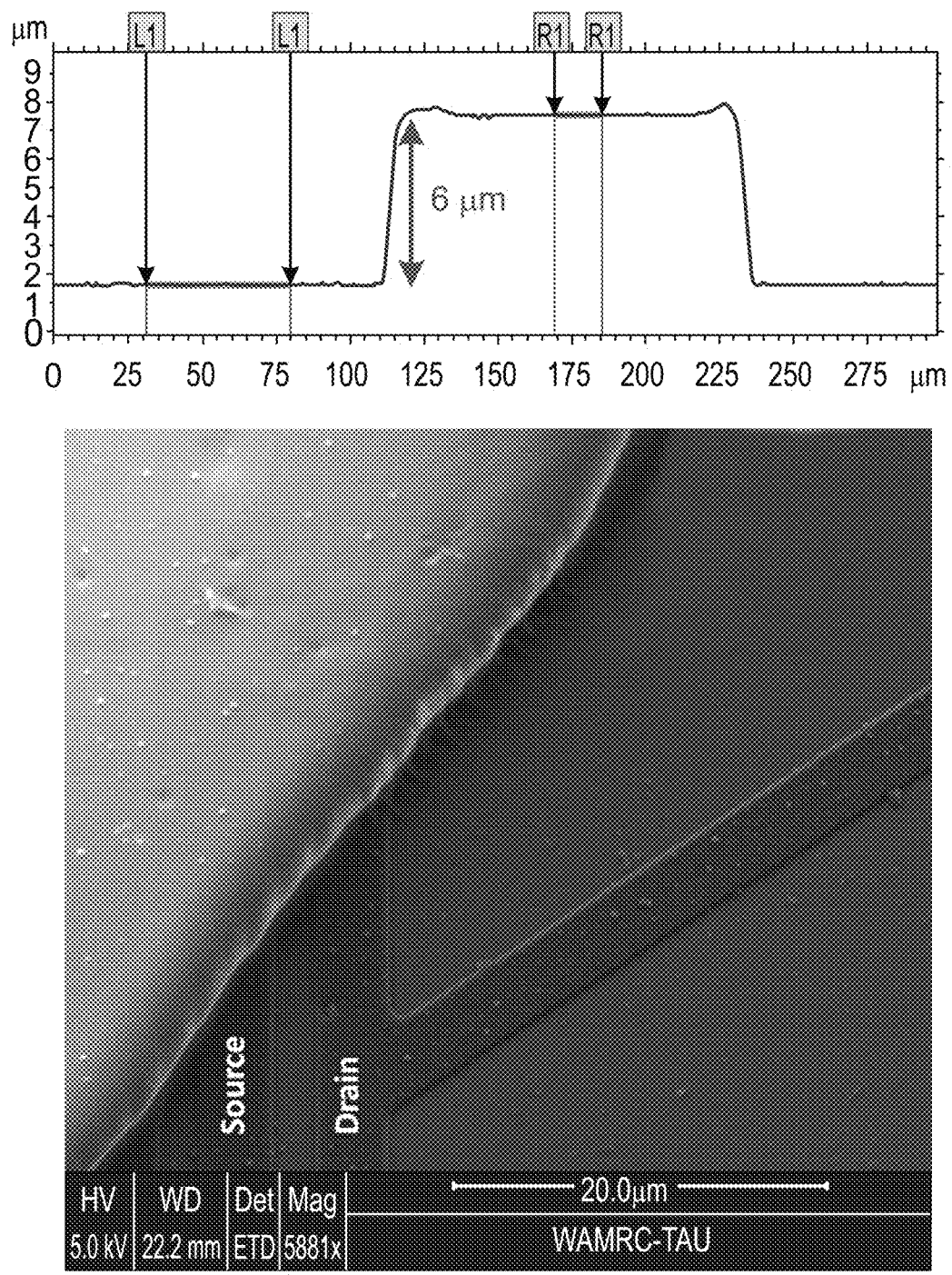

FIG. 4 presents a SEM image of a SiNW FET sensing system according to exemplary embodiments of the present invention, in which silicon nanowires are covered by a GOx-impregnated hydrogel film. Inset presents profilometer measurements of the GOx-hydrogel film on the SiNW FET system.

Figure 5:
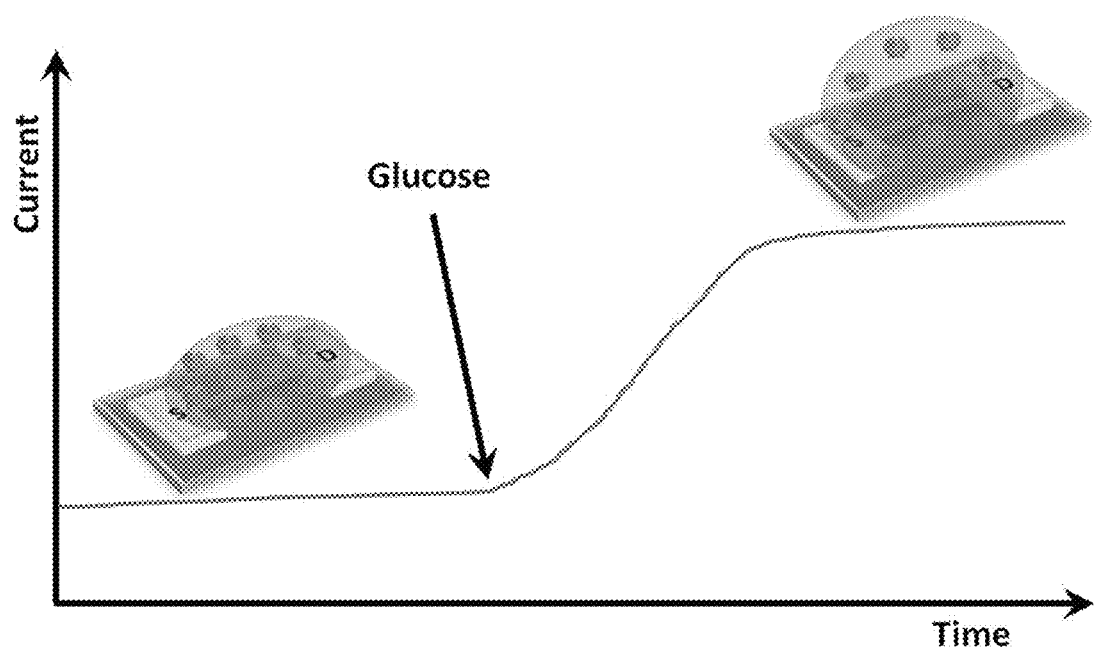

FIG. 5 presents an exemplary sensing of glucose by a GOx-impregnated hydrogel immobilized to a SiNW FET system as described in Example 2 and FIG. 3.

Figure 6:
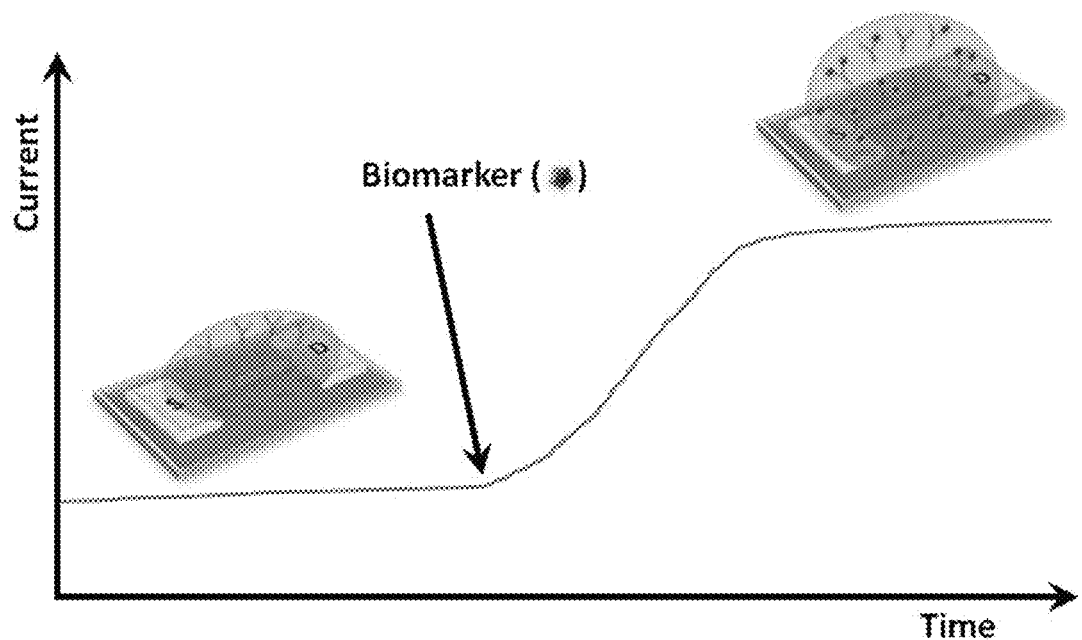

FIG. 6 presents a schematic illustration of an exemplary sensing of an antigen by a respective antibody-impregnated hydrogel immobilized to a SiNW FET system as described in Example 2.

Figure 7A:
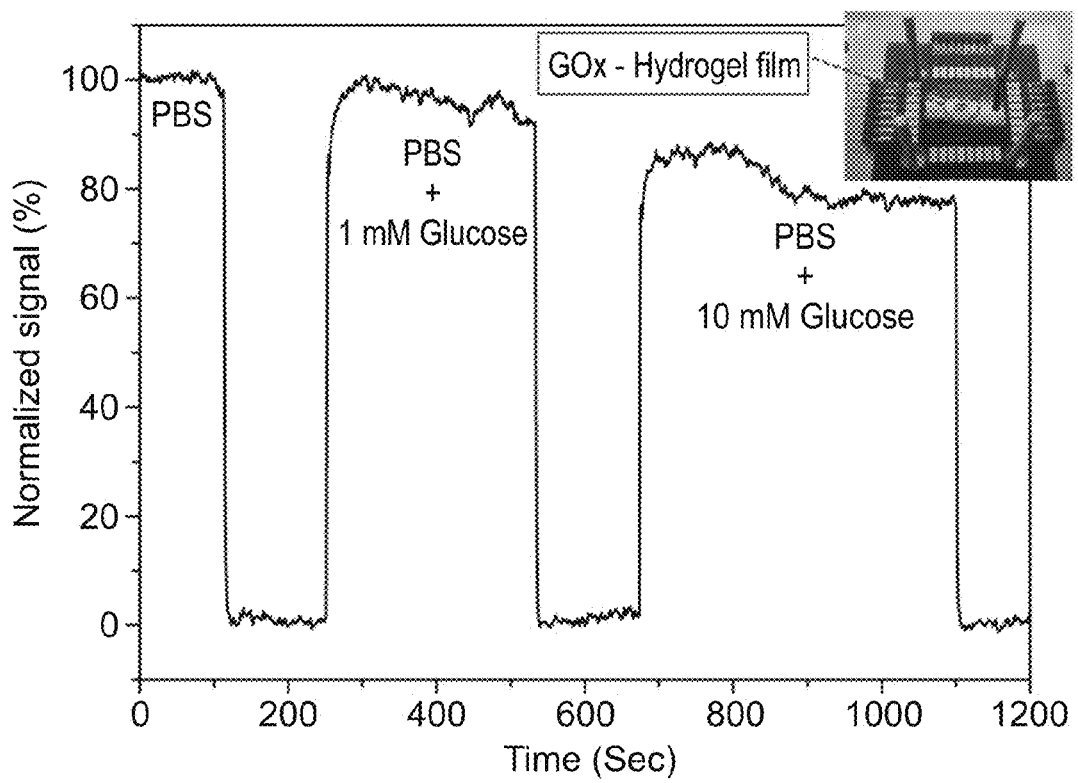
Figure 7B:
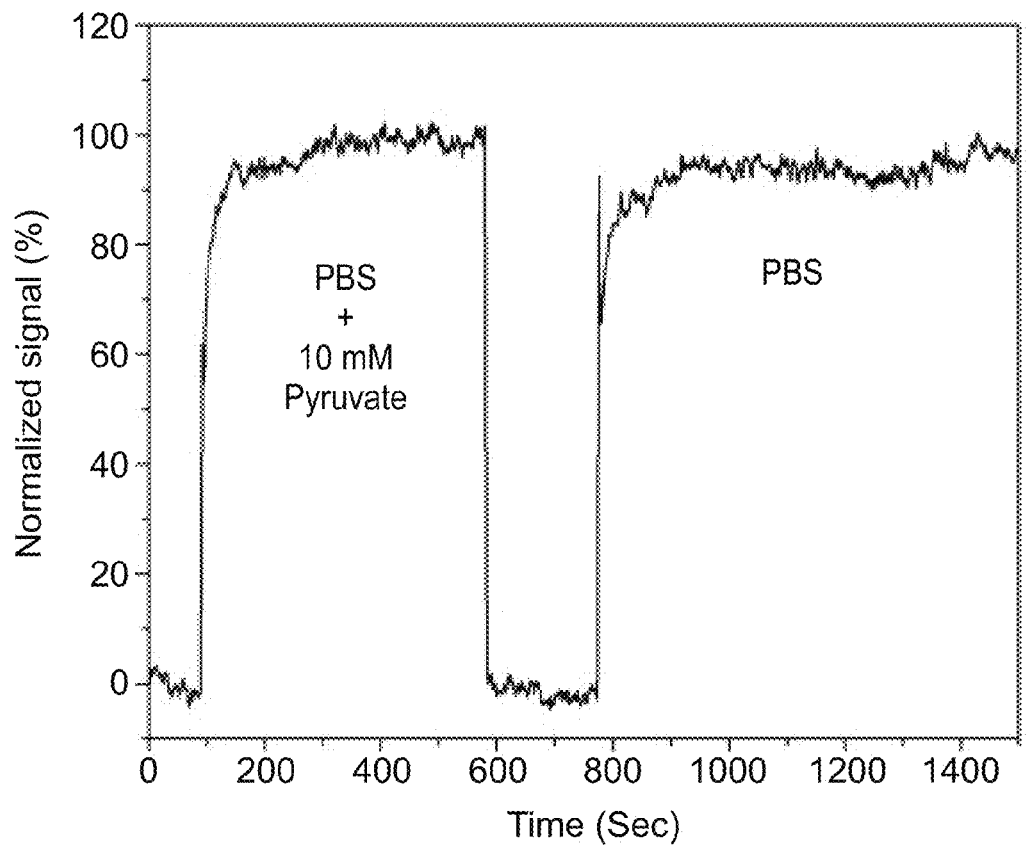

FIGS. 7A-B is a graph showing a normalized signal obtained upon contacting a SiNW chip system as shown in the inset, having with 200 SiNWs deposited on a printed circuit board, and covered with a hydrogel-GOx film (marked in red), with a 155 mM phosphate-buffered saline (PBS) solution per se, and containing 1 mM and 10 mM glucose (FIG. 7A), with a graph showing a normalized signal obtained upon contacting the same SiNW chip system with a 155 mM phosphate-buffered saline (PBS) solution containing pyruvate (FIG. 7B).

DESCRIPTION OF SPECIFIC EMBODIMENTS OF THE INVENTION

The present invention, in some embodiments thereof, relates to sensing and, more particularly, but not exclusively, to methods and systems for determining a presence and/or amount of analytes such as, but not limited to, bioanalytes, in a sample such as a biological sample, and to uses thereof.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have designed and successfully practiced a sensing system, which is usable in detecting and monitoring bioanalytes. The sensing system is usable, for example, in multiplex, optionally real-time and continuous, monitoring of bioanalytes in biological samples, both in vivo and ex-vivo. The sensing system is usable, for example, in monitoring metabolic activity in a physiological environment.

The sensing system of the present embodiments comprises at least one, preferably a plurality, of nanostructures, to which a sensing moiety which interacts with high specificity with a target bioanalyte is immobilized. The sensing moiety is immobilized by means of a hydrogel that is covalently attached to the nanostructures. The hydrogel is associated (e.g., impregnated) with the sensing moiety. As a result of an interaction between the sensing moiety and the bioanalyte, a detectable change in an electrical property of the nanostructure occurs, and thereby detection of a presence and/or amount of the bioanalyte is effected. The detectable change in the electrical property of the nanostructure(s) is due to a selective deformation, e.g., swelling or shrinkage and/or any other change in spatial distribution of molecules and/or charge in the hydrogel, of the hydrogel as a result of the specific interaction between the sensing moiety associated with the hydrogel and the respective bioanalyte. The deformation of the hydrogel, which is bound to the nanostructure's surface, leads to a change in an electrical property thereof, for example, a change in the charge density on the nanowire surface, which leads to a change in the conductivity.

The sensing systems of the present embodiments are highly sensitive, being capable of detecting analytes (target molecules) at a sub-picomolar concentration.

The sensing systems of the present embodiments enable fast detection of analytes, for example, within less than 10 minutes, or less than 5 minutes, or less, from contacting the sample.

The sensing systems of the present embodiments allow real-time and continuous monitoring of analytes, and are therefore usable in monitoring a presence and/or level of bioanalytes in a physiological environment (e.g., in vivo).

The sensing systems of the present embodiments circumvent the need of pre-processing the sample and allow analyzing biological samples without interfering with essential features and/or using hazardous agents.

The sensing systems of the present embodiments are further advantageously devoid of a labeling agent, and circumvent the use of spectroscopic measurements, which require additional time and instruments (e.g., for exciting and imaging).

The sensing systems of the present embodiments are capable of monitoring analytes in very small sample volumes.

The sensing systems of the present embodiments are further advantageously characterized by low-cost manufacturing, and, when the interaction of a sensing moiety with its respective analyte is reversible, are reusable, and therefore allow continuous monitoring.

The sensing system of the present embodiments can be integrated into systems comprising additional compartment in fluid communication with a sensing compartment that comprise the sensing system, through which a sample to be analyzed can be passed and/or a therapeutically active agent can be released. The additional compartments can be in fluid communication, for example, via microchannels, with the nanostructures.

The sensing system may comprise a plurality of nanostructures, forming, for example, an array, comprising different sensing moieties, thus enabling multiplex detection and monitoring of a variety of analytes.

The sensing system may be integrated into a lab-on-chip system, for use, for example, in points of care, for laboratory analyses (e.g., for analyzing blood samples), and for research purposes. The sensing system can alternatively be integrated into implantable devices or other configurations, for use in in vivo applications.

The sensing systems of the present embodiments thus allow fast and cheap detection of bioanalytes, such as metabolites, for handling chronic metabolic diseases like diabetes, or for personalized medicine of diseases associated with the bioanalytes, such as, but not limited to, cancer.

The sensing systems of the present embodiments can serve as efficient research tool in fields such as genomics, proteomics and bio-sensing.

Embodiments of the present invention relate to sensing systems and methods and to uses thereof in various diagnostic, therapeutic and research applications.

The Sensing System:

According to an aspect of some embodiments of the present invention there is provided a sensing system comprising a nanostructure and a hydrogel covalently attached to the nanostructure, the hydrogel having associated therewith a sensing moiety.

The sensing system, according to embodiments of the present invention, is configured for detecting (e.g., determining and/or monitoring) a presence and/or amount of an analyte in a sample, for example, a biological sample.

The sensing system is configured such that upon contacting the analyte, the nanostructure exhibits a detectable change in an electrical property.

According to some embodiments of the present invention, the system is configured such that when an analyte contacts the sensing moiety, a deformation of the hydrogel is effected, and this deformation leads to a change in an electrical property of the nanostructure to which the hydrogel is covalently attached.

Figure 1A:
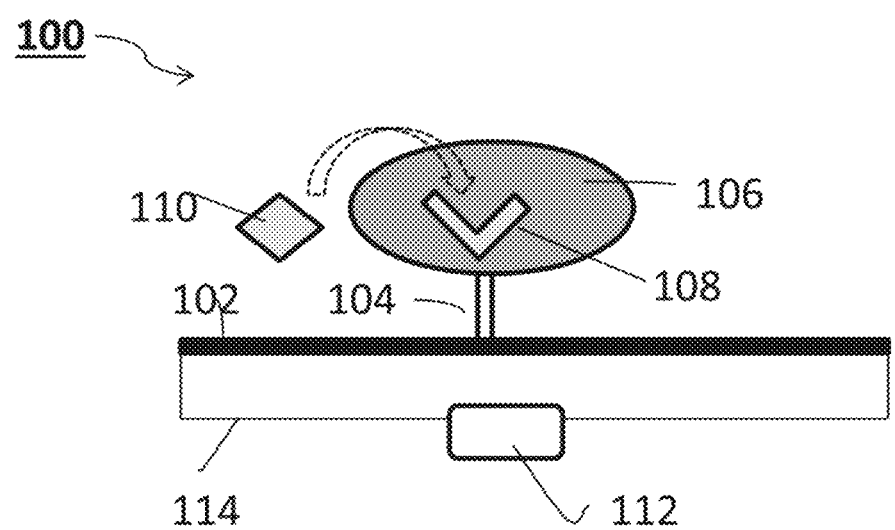

Referring now to the drawings, FIG. 1A is a schematic illustration of a sensing system 100 according to some embodiments of the present invention.

Figure 1B:
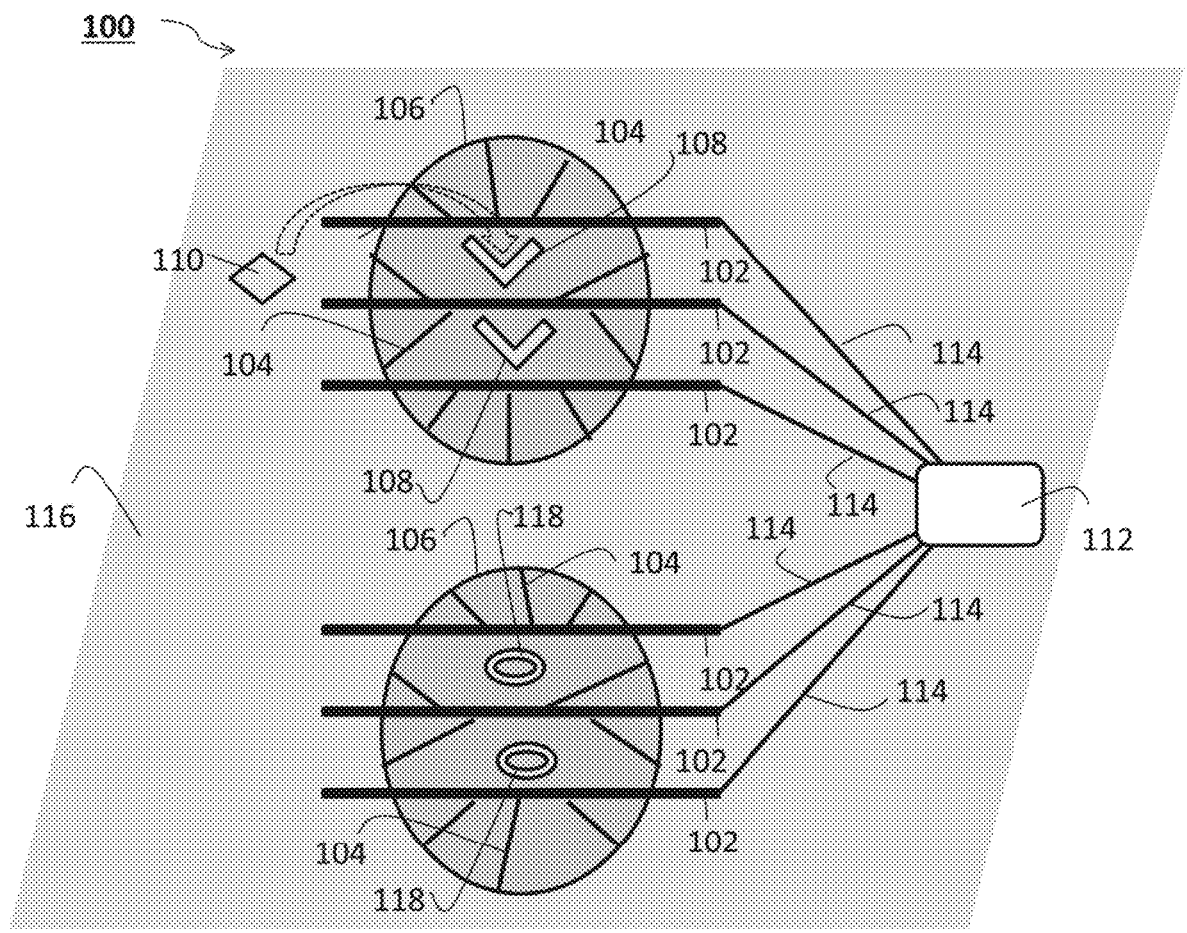

System 100 can comprise one or more nanostructure 102. Nanostructure 102 is preferably elongated. When a plurality (i.e., two or more) of nanostructures 102 is employed, the nanostructures 102 are optionally and preferably arranged in an array. For example, the nanostructures can be arranged generally parallel to each other, as illustrated in FIG. 1B.

As used herein, a "elongated nanostructure" generally refers to a three-dimensional body which is made of a solid substance, and which, at any point along its length, has at least one cross-sectional dimension and, in some embodiments, two orthogonal cross-sectional dimensions less than 1 micron, or less than 500 nanometers, or less than 200 nanometers, or less than 150 nanometers, or less than 100 nanometers, or even less than 70, less than 50 nanometers, less than 20 nanometers, less than 10 nanometers, or less than 5 nanometers. In some embodiments, the cross-sectional dimension can be less than 2 nanometers or 1 nanometer.

In some embodiments, the nanostructure has at least one cross-sectional dimension ranging from 0.5 nanometers to 200 nanometers, or from 1 nm to 100 nm, or from 1 nm to 50 nm.

The length of a nano structure expresses its elongation extent generally perpendicularly to its cross-section. According to some embodiments of the present invention the length of the nanostructure ranges from 10 nm to 50 microns.

The cross-section of the elongated nanostructure may have any arbitrary shape, including, but not limited to, circular, square, rectangular, elliptical and tubular. Regular and irregular shapes are included.

In various exemplary embodiments of the invention the nanostructure is a non-hollow structure, referred to herein as "nanowire".

A "wire" refers to any material having conductivity, namely having an ability to pass charge through itself.

In some embodiments, a nanowire has an average diameter that ranges from 0.5 nanometers to 200 nanometers, or from 1 nm to 100 nm, or from 1 nm to 50 nm.

In some embodiments of the present invention, the nanostructure is shaped as a hollow tube, preferably entirely hollow along its longitudinal axis, referred to herein as "nanotube" or as "nanotubular structure".

The nanotubes can be single-walled nanotubes, multi-walled nanotubes or a combination thereof.

In some embodiments, an average inner diameter of a nanotube ranges from 0.5 nanometers to 200 nanometers, or from 1 nm to 100 nm, or from 1 nm to 50 nm.

In case of multi-walled nanotubes, in some embodiments, an interval distance can range from 0.5 nanometers to 200 nanometers, or from 1 nm to 100 nm, or from 1 nm to 50 nm.

Selection of suitable materials for forming a nanostructure as described herein will be apparent and readily reproducible by those of ordinary skill in the art, in view of the guidelines provided herein for beneficially practicing embodiments of the invention. In some embodiments, the nanostructure of the present embodiments is a semiconductor nanostructure. A semiconductor nanostructure can be made of, for example, an elemental semiconductor of Group IV, and various combinations of two or more elements from any of Groups II, III, IV, V and VI of the periodic table of the elements.

As used herein, the term "Group" is given its usual definition as understood by one of ordinary skill in the art. For instance, Group III elements include B, Al, Ga, In and Tl; Group IV elements include C, Si, Ge, Sn and Pb; Group V elements include N, P, As, Sb and Bi; and Group VI elements include O, S, Se, Te and Po.

In some embodiments, the nanostructure is a carbon nanostructure, for example, a carbon nanotube.

In some embodiments of the present invention the nanostructure is made of a (e.g., semiconductor) material that is doped with donor atoms, known as "dopant". The present embodiments contemplate doping to effect both n-type (an excess of electrons than what completes a lattice structure lattice structure) and p-type (a deficit of electrons than what completes a lattice structure) doping. The extra electrons in the n-type material or the holes (deficit of electrons) left in the p-type material serve as negative and positive charge carriers, respectively. Donor atoms suitable as p-type dopants and as n-type dopants are known in the art.

For example, the nanostructure can be made from silicon doped with, e.g., B (typically, but not necessarily Diborane), Ga or Al, to provide a p-type semiconductor nanostructure, or with P (typically, but not necessarily Phosphine), As or Sb or to provide an n-type semiconductor nanostructure.

In some embodiments, the sensing system comprises a plurality of nanowires and/or nanotubes, grown on a substrate by using, for example, chemical vapor deposition. Optionally, once the nanowires and/or nanotubes are obtained, the substrate is etched (e.g., by photolithography) and the nanowires and/or nanotubes are arranged within the sensing compartment as desired. Alternatively, nanowires can be made using laser assisted catalytic growth (LCG). Any method for forming a nanostructure and of constructing an array of a plurality of nanostructures as described herein is contemplated.

In some embodiments, the sensing system comprises a plurality of nanostructures, e.g., from 2 to 2000 nanostructures per 1 square centimeter. The nanostructures can comprise nanowires, as described herein, nanotubes, as described herein, and combination thereof.

Exemplary nanotubes and methods of preparing same are disclosed in WO 2010/052704, which is incorporated by reference as if fully set forth herein.

Any other (e.g., semiconductor) nanostructures, as described in further detail hereinbelow, are also contemplated.

Sensing system 100 further comprises a hydrogel 106 covalently attached to nanostructure 102, optionally and preferably via linker 104. Hydrogel 106 is selected such that upon contacting with an analyte (e.g., a bioanalyte) 110 nanostructure 102 exhibits a detectable change in an electrical property of nanostructure 102. Hydrogel 106 can be attached to nanostructure 102 via a plurality (e.g., 2 or more) linkers 104. Hydrogel 106 can be attached to a plurality of nanostructures 102 via a plurality of linkers 104.

Hydrogel 106 has associated therewith a sensing moiety 108 which selectively interacts with analyte 110, as described in further detail hereinafter. Sensing moiety 108 is associated with hydrogel 106, which is attached to nanostructure 102, as is described in further detail hereinafter.

By "associated with" it is meant that hydrogel 106 and sensing moiety 110 are at least in physical interaction, such that sensing moiety 108 is incorporated in and/or on hydrogel 106. Sensing moiety 108 can be absorbed to the surface of hydrogel 106, or, preferably, sensing moiety 108 is entrapped (impregnated) in hydrogel 106.

Upon interacting with analyte 110, hydrogel 106 exhibits a deformation, leading to a change in electrical property of nanostructure 102.

For example, nanostructure 102 can exhibit a change in density of electrons or holes over some region of nanostructure 102 or over the entire length of nanostructure 102. As a result, nanostructure 102 exhibits, for example, a change in its conductivity or resistivity.

The deformation can be expressed in terms of a deformation parameter such as, but not limited to, a change in volume, a change in length (e.g., diameter), a change in surface area, a change in contact area with the substrate, a change in contact area with the nanostructure 102, and a change of the shape of hydrogel 106.

The changed parameter typically depends on the type of interaction between sensing moiety 108 and analyte 110.

In some embodiments, the deformation comprises a change in a volume of the hydrogel. Upon interacting with analyte 110, hydrogel 106 can exhibits, for example, a volume increment (e.g., swelling) or a volume decrement (e.g., shrinkage). A change in the volume of hydrogel 106 induces a change in an electrical property of nano structure 102.

In some embodiments, the deformation comprises a change in a spatial distribution of molecules and/or charge in hydrogel 106.

In some embodiments, the changed parameter is a change in a spatial distribution of molecules and/or charge in hydrogel 106.

A change in a spatial distribution of molecules in hydrogel 106 can be, for example, a change in an intermolecular distance between molecules forming hydrogel 106.

Such a change can result from, for example, accumulation of analyte 110 in hydrogel 106. For example, when analyte 110 is a biomolecule such as a protein (e.g., antigen) or an oligonucleotide, its accumulation in hydrogel 106 due to its binding with sensing moiety 108 changes an intermolecular distance between the hydrogel's molecules. In another example, when analyte 110 interacts with sensing moiety 108 such that a chemical reaction occurs and reaction products are formed, a presence of such reaction products induces a change in intermolecular distance in the hydrogel molecules. A change in an intermolecular distance between hydrogel molecules in proximity to a surface of nanostructure 102 results in a change in an electrical property of nanostructure 102, as described herein Alternatively, or in addition, a change in a spatial distribution of molecules in hydrogel 106 can be, for example, a change in a concentration of molecules other than the molecules forming hydrogel 106.

For example, diffusion of analyte 110 into hydrogel 106 may involve reaction products formed upon interaction between sensing moiety 108 and analyte 110, and a formation of such reaction products results in elevated concentration of the reaction products. Such a change in a concentration of said reaction products in proximity to a surface of nanostructure 102 induces a change in an electrical property of nanostructure 102.

When such reaction products are charged species (e.g., an acid, a base, a cation, an anion), a change in concentration of such molecules also results in a change in a charge distribution in hydrogel 106.

A change in a charge distribution of molecules in hydrogel 106 can, for example, result from a change in pH of the hydrogel, that is, a change in a concentration of proton molecules in the hydrogel. A change in a pH of hydrogel 106 may result from an interaction between analyte 110 and sensing moiety 108 (for example, a chemical reaction that results in formation of an acid), or when analyte 110 by itself comprises acidic or alkaline moieties.

A change in a charge distribution of molecules in hydrogel 106 can alternatively, or in addition, result from a change in a concentration of charges species in the hydrogel 106. Such a change in concentration of charges species may result from analyte 110 comprising by itself charged species, and/or due to formation of charges species as a result from an interaction between analyte 110 and sensing moiety 108.

The change in spatial distribution of molecules and/or charge in hydrogel 106 upon interacting with analyte 110 can be from about 5% to about 80%, or from about 5% to about 50%, including any intermediate values and subranges therebetween.

In some embodiments, hydrogel 106 is in a form of a hydrogel nanoparticle.

FIG. 1B presents an embodiment of system 100 which comprises a plurality of nanostructures. According to some embodiments of the present invention, sensing system 100 comprises a plurality of nanostructures 102 arranged as an array, preferably parallel to one another, as shown in FIG. 1B.

Hydrogel 106 can be attached to a plurality of nanostructures 102 via a plurality of linkers 104. Hydrogel 106 can be attached to each nanostructure via one linker 104, or via a plurality of linkers 104, as exemplified in FIG. 1B. In some embodiments, hydrogel 106 forms a film on the array of nano structures 102, which is attached to a plurality of nanostructures 102 via linkers 104.

In embodiments where hydrogel 106 is a hydrogel nanoparticle, a hydrogel nanoparticle or a plurality of nanoparticles can be covalently attached to each nanostructure, or a hydrogel nanoparticle can be attached to two or more nanoparticles.

When a plurality of nanostructures 102 is employed, all the nanostructures can be covalently attached to the same hydrogel, which is associated with sensing moiety 108. Alternatively, and as illustrated in FIG. 1B, one portion of nanostructures 102 is attached to hydrogel 106 associated with sensing moiety 108, and at least one other portion of nanostructures 102 is attached to hydrogel 106 associated with moiety 118 which is different from sensing moiety 108. Moiety 118 can be a sensing moiety, different from sensing moiety 108, and selectively interacting with a different analyte, and therefore enables detection of a plurality of analytes, sequentially or simultaneously. Alternatively, moiety 118 is a non-sensing moiety, as described herein, used for self-calibration of sensing system 100 in a physiological environment, as described in further detail hereinafter (see, Example 4).

The change in the property of nanostructure(s) 102 in system 100 (FIGS. 1A and 1B) can be detected by a detector 112 which communicates with nanostructure 102 via a communication line 114. When a plurality of nanostructures is employed, each of the nanostructures preferably communicates with detector 112 over a separate communication channel.

Detector 112 can be of any type that allows detection of electrical (e.g., semiconductor) property.

For example, detector 112 can be constructed for measuring an electrical measure corresponding to a change in the electrical property. The electrical measure can be, e.g., voltage, current, conductivity, resistance, impedance, inductance, charge, etc.

The detector typically includes a power source and a voltmeter or amperometer. In some embodiments a conductance change of less than 10,000 nS can be detected, in some embodiments a conductance change of less than 1,000 nS can be detected, in some embodiments a conductance change of less than 100 nS can be detected, in some embodiments a conductance change of less than 10 nS can be detected, and in some embodiments a conductance change of less than 1 nS can be detected.

For example, when an interaction between analyte 110 and sensing moiety 108 effects a change in a parameter of hydrogel 106, and a change in this parameter effects a change in electron or hole density of nanostructure 102, detector 112 can be configured to apply voltage to nanostructure 102 and to measure the current through nanostructure 102. In some embodiments of the present invention nanostructure 102 is in contact with a source electrode and a drain electrode (not shown, see FIG. 1C). In these embodiments, detector 112 is optionally and preferably configured to apply a source-drain voltage between the source electrode and the drain electrode and to measure changes in the source-drain current. In some embodiments of the present invention nanostructure 102 is in contact with a source electrode, a drain electrode and a gate electrode, such that nanostructure 102 forms a transistor, such as, but not limited to, a field effect transistor (FET). In these embodiments, detector 112 is optionally and preferably configured to apply a source-drain voltage between the source electrode and the drain electrode and optionally also a gate voltage to the gate electrode, and to measure changes in the source-drain current.

Figure 1C:
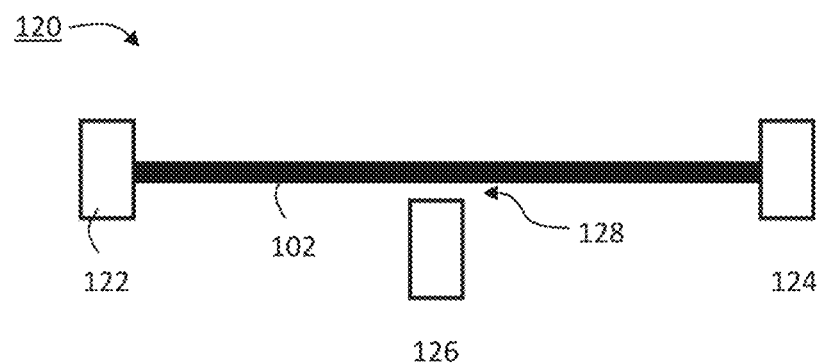

FIG. 1C is a schematic illustration of nanostructure 102 in embodiment in which nanostructure 102 forms a transistor 120 (e.g., FET). Transistor 120 comprises a source electrode 122, a drain electrode 124, a gate electrode 126 wherein nanostructure 102 serves as a channel. A gate voltage can be applied to channel nanostructure 102 through gate electrode 126. The gate electrode 126 is optionally and preferably, but not necessarily, spaced apart from nanostructure 102 by a gap 128. In some embodiments, when the voltage of gate electrode 126 is zero, nanostructure 102 does not contain any free charge carriers and is essentially an insulator. As the gate voltage is increased, the electric field caused thereby attracts electrons (or more generally, charge carriers) from source electrode 122 and drain electrode 124, and nanostructure 102 becomes conducting. In some embodiments, no gate voltage is applied and the change in the charge carrier density is effected solely by virtue of the interaction between sensing moiety 108 and analyte 110.

It is appreciated that when the electrical property of the nanostructure varies in response to interaction with a sample that contains the analyte, a detectable signal can be produced. For example, a change in the electrical property of the channel induces a change in the characteristic response of the transistor to the gate voltage (e.g., the source-drain current as a function of the gate voltage), which change can be detected and analyzed.

Nanostructure(s) 102 can be deposited onto, or be partially or fully submerged in, a substrate 116 (shown in FIG. 1B).

The substrate can be, for example, an elastomeric polymer substrate. Suitable elastomeric polymer substrate materials are generally selected based upon their compatibility with the manufacturing process (soft lithography, stereo lithography and three-dimensional jet printing, etc.) and the conditions present in the operation to be performed. Such conditions can include, for example, extremes of pH, pressure (e.g., in case the substrate features microchannels), temperature, ionic concentration, and the like. Additionally, elastomeric polymer substrate materials are also selected for their inertness to critical components of an analysis or synthesis to be carried out by the system. Elastomeric polymer substrate materials can also be coated with suitable materials.

Representative examples of elastomeric polymers include, without limitation, polydimethylsiloxane (PDMS), polyisoprene, polybutadiene, polychloroprene, polyisobutylene, poly(styrene-butadiene-styrene), polyurethanes and silicones.

Various embodiments of the hydrogel (e.g., hydrogel 106 shown in FIGS. 1A and 1B), the linker (e.g., linker 104 shown in FIGS. 1A and 1B), the sensing moiety (e.g., sensing moiety 108 shown in FIGS. 1A and 1B and/or sensing moiety 118 shown in FIG. 1B), the analyte (e.g., analyte 110 shown in FIGS. 1A and 1B), and the interaction therebetween, and of optional additional components of the sensing system of the present embodiments are provided hereinbelow.

The Hydrogel and Linker:

Herein and in the art, the term "hydrogel" describes a three-dimensional fibrous network containing at least 20%, typically at least 50%, or at least 80%, and up to about 99.99% (by mass) water. A hydrogel can be regarded as a material which is mostly water, yet behaves like a solid or semi-solid due to a three-dimensional crosslinked solid-like network, made of natural and/or synthetic polymeric chains, within the liquid dispersing medium. According to some embodiments of the present invention, a hydrogel may contain polymeric chains of various lengths and chemical compositions, depending on the precursors used for preparing it. The polymeric chains can be made of monomers, oligomers, block-polymeric units, which are inter-connected (crosslinked) by chemical bonds (covalent, hydrogen and ionic/complex/metallic bonds, typically covalent bonds). The network-forming material comprises either small aggregating molecules, particles, or polymers that form extended elongated structures with interconnections (the crosslinks) between the segments. The crosslinks can be in the form of covalent bonds, coordinative, electrostatic, hydrophobic, or dipole-dipole interactions or chain entanglements between the network segments. In the context of the present embodiments, the polymeric chains are preferably hydrophilic in nature.

The hydrogel, according to embodiments of the present invention, can be of biological origin or synthetically prepared.

According to some embodiments of the present invention, the hydrogel is biocompatible, and is such that when a biological moiety is impregnated or accumulated therein, an activity is the biological moiety is maintained, that is, a change in an activity of the biological moiety is no more than 30%, or no more than 20%, or no more than 10%, compared to an activity of the biological moiety in a physiological medium. The biological moiety can be sensing moiety 108 or analyte 110.

Exemplary polymers or co-polymers usable for forming hydrogel 106 according to the present embodiments include polyacrylates, polymethacrylates, polyacrylamides, polymethacrylamides, polyvinylpyrrolidone and copolymers of any of the foregoing. Other examples include polyethers, polyurethanes, and poly(ethylene glycol), functionalized by cross-linking groups or usable in combination with compatible cross linking agents.

Some specific, non-limiting examples, include: poly(2-vinylpiridine), poly(acrylic acid), poly(methacrylic acid), poly(N-isopropylacrylamide), poly(N,N'-methylenbisacrylamide), poly(N—(N-propyl)acrylamide), poly(methacyclic acid), poly(2-hydroxyacrylamide), poly(ethylene glycol) acrylate, poly(ethylene glycol)methacrylate, and polysaccharides such as dextran, alginate, agarose, and the like, and any co-polymer of the foregoing.

Hydrogel precursors forming such polymeric chains are contemplated, including any combination thereof.

Hydrogels are typically formed of, or are formed in the presence of, di- or tri- or multi-functional monomers, oligomer or polymers, which are collectively referred to as hydrogel precursors or hydrogel-forming agents, having two, three or more polymerizable groups. The presence of more than one polymerizable group renders such precursors crosslinkable, and allow the formation of the three-dimensional network.

Exemplary crosslinkable monomers include, without limitation, the family of di- and triacrylates monomers, which have two or three polymerizable functionalities, one of which can be regarded as a crosslinkable functional group. Exemplary diacrylates monomers include, without limitation, methylene diacrylate, and the family of poly(ethylene glycol)$_n$ dimethacrylate (nEGDMA). Exemplary triacrylates monomers include, without limitation, trimethylolpropane triacrylate, pentaerythritol triacrylate, tris (2-hydroxy ethyl) isocyanurate triacrylate, isocyanuric acid tris(2-acryloyloxyethyl) ester, ethoxylated trimethylolpropane triacrylate, pentaerythrityl triacrylate and glycerol triacrylate, phosphinylidynetris(oxyethylene) triacrylate.

Hydrogels may take a physical form that ranges from soft, brittle and weak to hard, elastic and tough material. Soft hydrogels may be characterized by rheological parameters including elastic and viscoelastic parameters, while hard hydrogels are suitably characterized by tensile strength parameters, elastic, storage and loss moduli, as these terms are known in the art.

The softness/hardness of a hydrogel is governed inter alia by the chemical composition of the polymer chains, the "degree of crosslinking" (number of interconnected links between the chains), the aqueous media content and composition, and temperature.

A hydrogel, according to some embodiments of the present invention, may contain macromolecular polymeric and/or fibrous elements which are not chemically connected to the main crosslinked network but are rather mechanically intertwined therewith and/or immersed therein. Such macromolecular fibrous elements can be woven (as in, for example, a mesh structure), or non-woven, and can, in some embodiments, serve as reinforcing materials of the hydrogel's fibrous network. Non-limiting examples of such macromolecules include polycaprolactone, gelatin, gelatin methacrylate, alginate, alginate methacrylate, chitosan, chitosan methacrylate, glycol chitosan, glycol chitosan methacrylate, hyaluronic acid (HA), HA methacrylate, and other non-crosslinked natural or synthetic polymeric chains and the likes. According to some of any of the embodiment of the present invention, the amount of such non-crosslinked additives is small and typically does not exceed 100 mg in 1 ml of the hydrogel-forming precursor solution.

In some embodiments, the hydrogel is porous and in some embodiments, at least a portion of the pores in the hydrogel are nanopores, having an average volume at the nanoscale range.

In some of any of the embodiments described herein, the hydrogel is covalently attached to the nanostructure's surface by means of covalent bonds formed between the hydrogel and compatible reactive groups on the surface of the nanostructures, directly or via a linker.

Reactive groups on the nanostructure's surface are either intrinsic or can be generated upon a suitable treatment. In some embodiments, where the nanostructure is SiNW or silicon nanotubes, free hydroxyl groups are intrinsically present on the surface of the nanostructures and can be utilized for attaching functional moieties thereto.

Alternatively, the nanostructures described herein are first surface-modified so as to generate surface reactive groups. Such a surface modification can be performed by, for example, attaching to intrinsic functional groups on the nanostructure surface a bifunctional linker molecule, which comprises in one terminus thereof a reactive group that is capable of forming a bond with these intrinsic functional groups and in another terminus thereof a reactive group that can covalently attach to the hydrogel.

In some embodiments, the hydrogel is attached to the nanostructure via a bifunctional linker, as described herein.

An exemplary such a linker is derived from a silyl that comprises 1, 2 or 3-living groups that allows the silyl to interact with intrinsic hydroxyl groups on the silicon nanostructure surface, forming —Si—O—Si bonds, and 1, 2 or 3 hydrocarbon groups (e.g., alkyl, alkylene, cycloalkyl, aryl)

terminating with a reactive group that is capable of covalently attaching to the hydrogel.

Alternatively, the linker can be derived from an orthosilicate that comprises 1, 2, or 3 OR' groups, with can interact with intrinsic hydroxyl groups on the silicon nanostructure surface, forming —Si—O—Si bonds, and 1, 2 or 3 hydrocarbon groups (e.g., alkyl, alkylene, cycloalkyl, aryl) terminating with a reactive group that is capable of covalently attaching to the hydrogel.

In exemplary embodiments, the reactive group is a polymerizable group that is chemically compatible with one or more polymerizable groups of at least one hydrogel precursor, such that the linker (linking moiety) forms a part of the hydrogel.

For example, if the hydrogel is made of polyacrylate chains, and is formed of di-acrylate and/or tri-acrylate precursors as described herein, a suitable linker is derived from a silyl or orthosilicate that comprises one or more hydrocarbon chains, at least one terminating with an acrylate group. The acrylate group polymerizes/cross-links along with the acrylate groups of the hydrogel precursor, resulting is covalent attachment of the hydrogel to the nanostructure's surface.

In some embodiments, when the linker comprises a hydrocarbon chain, which can be of any length. For example, the hydrocarbon chain can be of 1 to $10^6$, or of 1 to $10^3$, or from 1 to 100, or from 1 to 50, or from 1 to 20, or from 1 to 10, carbon atoms in length, including any intermediate values and subranges therebetween.

In exemplary embodiments, the linker is derived from halosilylalkyl (e.g., trichlorosilylalkyl) comprising an alkyl terminating with an acrylate group.

In exemplary embodiments, the linker is derived from alkoxysilylalkyl (e.g., trialkoxysilylalkyl) comprising an alkyl terminating with an acrylate group.

In some of these embodiments, the alkyl is propyl. Other alkyls, for example, ethyl, butyl, pentyl, and hexyl, and higher alkyls are also contemplated.

The Sensing Moiety and the Analyte:

The sensing systems according to the present embodiments are operable based on a selective (specific) interaction between an analyte and a sensing moiety that selectively interacts with the analyte.

Herein throughout, the term "analyte" is also referred to interchangeably as "target analyte" or "target molecule", and encompasses chemical and biological species, including small molecules and biomolecules such as, but not limited to, peptides, proteins, nucleotides, oligonucleotides, and polynucleotides.

In some embodiments, the sample is a biological sample, as described herein, and the analyte is a bioanalyte, that is, a chemical or biological species that is present in biological systems, for example, a biological system of a subject, as defined herein.

In some embodiments, the bioanalyte is a biomarker.

The term "biomarker" describes a chemical or biological species which is indicative of a presence and/or severity of a disease or disorder in a subject. Exemplary biomarkers include small molecules such as metabolites, and biomolecules such as antigens, hormones, receptors, and any other proteins, as well as polynucleotides. Any other species indicative of a presence and/or severity of medical conditions are contemplated.

The sensing moiety usable in the sensing systems as described herein is a chemical or biological moiety that selectively interacts with the analyte. The interaction between the sensing moiety and the analyte typically involves binding, and may further involve activation and/or chemical interaction such as chemical reaction.

By "selectively interacts" it is meant that the sensing moiety binds to the analyte at a much higher level than to another, even structurally or functionally similar, species. In some embodiments, the sensing moiety is such that a binding affinity of the sensing moiety and the analyte is characterized by a dissociation constant, Kd, of no more than 1 mM, or no more than 100 nM, or no more than 10 nM, or no more than 1 nM, or no more than $10^{-10}$M, or no more than $10^{-12}$M, and even lower, e.g., as low as $10^{-15}$M.

The interaction between the sensing moiety and the analyte can be reversible or irreversible, and is preferably reversible.

In some of any of the embodiments described herein, the analyte and the sensing moiety form an affinity pair, as defined herein.

In some embodiments, the analyte is a bioanalyte, e.g., a biomarker, as described herein, and the sensing moiety is an analyte specific reagent, as defined by the FDA (see, (ASRs) in 21 CFR 864.4020).

In some embodiments, the bioanalyte and the sensing moiety form an affinity pair, characterized by a dissociation constant, $K_D$ lower than $10^{-5}$ M, or lower than than $10^{-7}$ M, or lower than $10^{-8}$ M, than $10^{-9}$, or than $10^{-10}$ M.

Exemplary affinity pairs include, without limitation, an enzyme-substrate pair, a polypeptide-polypeptide pair (e.g., a hormone and receptor, a ligand and receptor, an antibody and an antigen, two chains of a multimeric protein), a polypeptide-small molecule pair (e.g., avidin or streptavidin with biotin, enzyme-substrate), a polynucleotide and its cognate polynucleotide such as two polynucleotides forming a double strand (e.g., DNA-DNA, DNA-RNA, RNA-DNA), a polypeptide-polynucleotide pair (e.g., a complex formed of a polypeptide and a DNA or RNA e.g., aptamer), a polypeptide-metal pair (e.g., a protein chelator and a metal ion), a polypeptide and a carbohydrate (leptin-carbohydrate), and the like.

In the context of the present embodiments, one member of an affinity pair is an analyte and the other is the sensing moiety.

In some embodiments, the sensing moiety is an enzyme and the analyte is the enzyme's substrate.

In some embodiments, the analyte is a metabolite and the enzyme is a redox enzyme (e.g., an oxidase or reductase) specific to the metabolite.

In some embodiments, the metabolite is glucose, and the enzyme is glucose oxidase, abbreviated herein as GOx or GOX.

In some embodiments, the metabolite is lactate, and the enzyme is lactate oxidase.

In some embodiments, the metabolite is pyruvate, and the enzyme is pyruvate oxidase.

In some embodiments, the metabolite is Hypoxanthine, and the enzyme is xanthine oxidase;

In some embodiments, the metabolite is NAD(P)H, and the enzyme is NAD(P)H oxidase;

In some embodiments, the metabolite is Superoxide ($O_2^-$), and the enzyme is superoxide dismutase.

In some embodiments, the metabolite is an aldehyde, and the enzyme is a respective aldehyde oxidase.

Additional examples include oxidases such as beta-galactosidase, alkaline phosphatase, and beta-glucoronidase, and their respective substrates.

Additional examples include enzymes such as reductases and dehydrogenases and their respective substrates.

In some embodiments, the analyte is a protein biomarker, for example, a receptor or an antigen, and the sensing moiety is a ligand of the protein, for example, a receptor ligand or an antibody, respectively.

In some embodiments, the analyte is an antigen and the sensing moiety is an antibody or a fragment thereof having a high affinity, as defined herein, to the antigen.

In an exemplary embodiment, the antigen is cardiac troponin I and the sensing moiety is an anti-cardiac troponin I. Any other antigen-antibody pairs are contemplated.

Additional Components:

The sensing system (e.g., sensing system 100) as described herein can be integrated with other components or compartments or into other systems.

According to an aspect of some embodiments of the present invention the sensing system is integrated into a system which comprises at least one sensing compartment that comprises a sensing system of the present embodiments, and at least one additional compartment.

In some embodiments, the sensing system (e.g., sensing system 100) is integrated into a microfluidic system.

Figure 1D:
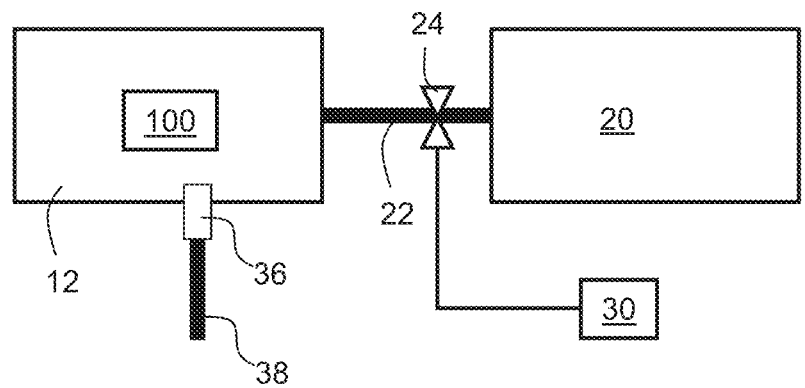

FIG. 1D is a schematic illustration of a system 300 incorporating sensing system 100 in a sensing compartment 12. System 300 comprises a compartment 20 in (e.g., fluid) communication with sensing compartment 12. System 300 can comprise two or more compartments 20, being in communication thereamongst and/or with sensing compartment 12.

In some embodiments, system 300 is a microfluidic system, and the compartments are in fluid communication thereamongst.

One or more of compartment 20 can be a chamber.

The term "chamber" as used herein refers to a close or open enclosure configured to contain a fluid (e.g., a sample solution, a reagent solution).

In some embodiments, compartment 20 is a chamber as described herein is configured to contain an amount of fluid in a range of from microliters to milliliters.

In some embodiments, compartment 20 is a chamber in a form of a well.

Compartment 20 can be in fluid communication with the sensing system by means of microchannels 22, for example, microchannels within a substrate onto which nanostructures 102 in sensing system 100 are deposited (e.g., substrate 116 shown in FIG. 1B). Compartment 20 can be positioned above the surface of the microchannels or within the surface of the microchannels. If a plurality of compartments is employed, each compartment can independently adopt any of the configurations described herein.

The term "microchannel" as used herein refers to a fluid channel having cross-sectional dimensions the largest of which being less than 1 mm, more preferably less than 500 µm, more preferably less than 400 µm, more preferably less than 300 µm, more preferably less than 200 µm, e.g., 100 µm or smaller.

The microchannels and the compartments (e.g., sensing compartment 12 and compartment 20) can all be formed in a substrate, which can be the same substrate that supports the nanostructures (nanostructures 102 in sensing system 100) or it can be a different substrate, as desired.

In some embodiments, the microfluidic system (e.g., system 300) comprises compartment 20 in a form of a chamber which is configured for containing at least a portion of the sample. That is, the sample, or a portion thereof, is introduced into compartment 20 and is then introduced (e.g., by means of the microchannels) to sensing compartment 12 comprising sensing system 100. Such a compartment is also referred to herein as sample compartment or sample chamber.

Alternatively, or in addition, system 300 comprises compartment 20 (e.g., in a form of a chamber) which is configured for containing a therapeutically active agent (a drug). In some embodiments, compartment 20 is configured to release the drug. In some embodiments, compartment 20 is configured to controllably release the drug is response to the change in electrical property detected upon contacting analyte 110 with sensing moiety 108 in sensing system 100. Such a compartment is also referred to herein as a drug compartment or drug chamber.

System 100 is optionally and preferably incorporated in one or more sensing compartments 12 (only one sensing compartments 12 is illustrated in FIG. 1D for clarity of presentation). In some of any of the embodiments a plurality of sensing systems 100 are included in the same sensing compartment and are in fluid communication thereamongst at all times. In some of any of the embodiments the sensing systems are included in two or more sensing compartments and, in each sensing compartment the plurality of nanostructures are in fluid communication thereamongst at all times. Alternatively, compartment 20 can be an additional sensing compartment, which comprises a sensing system which can be the same as or different from sensing system 100.

When two or more sensing systems 100 are included, the sensing systems can differ from one another by the type of sensing moiety or the moiety incorporated in the hydrogel or by the type of nanostructures. For example, one sensing system can include a sensing moiety for detecting a first analyte, and one sensing system can include a sensing moiety for detecting a second analyte being different from the first analyte, and so forth. In another example, one sensing system can be system 100 which includes a sensing moiety and one sensing system can be a similar sensing system, but including a non-sensing moiety, as described herein, for e.g., self-calibration. For example, one sensing system can include nanostructures 102 shown in FIG. 1B with sensing moiety 108 and one sensing system can include nanostructures 102 shown in FIG. 1B with moiety 118.

Sensing compartment 12 and compartment 20 are optionally and preferably connected via a microchannel 22 providing fluid communication therebetween. In some embodiments of the present invention system 300 comprises a construable valve 24 for establishing and disestablishing the fluid communication. When there is more than one sensing compartment 12, all of the sensing compartment are optionally and preferably connected to the same compartment via a respective plurality of microchannels. Alternatively, system 300 can comprise more than one compartment in which at least two sensing compartments are connected via microchannels to at least two different compartments. Typically, but not necessarily, microchannels 22 engage the same plane. For example, compartment 12, microchannel 22 and compartment 20 can all be formed in the substrate such that microchannels 22 engage the same plane over the substrate.

Microchannels 22 can be formed in a substrate (e.g., substrate 116 shown in FIG. 1B) by any technique known in the art, including, without limitation, soft lithography, hot embossing, stereolithography, three-dimensional jet printing, dry etching and injection molding.

In some embodiments of the present invention the sensing compartment, the microchannels and the other compartments are formed on the same substrate, and in some embodiments of the present invention the sensing compartment is formed on a different substrate than the microchannels and the other compartments. When different substrates are used, the different substrates can be connected or be separated in a manner than maintains the controllable fluid communication between the sensing compartment and the other compartments. For example, controllable fluid communication between the two separate substrates can be ensured by a conduit. When sensing compartment and the other compartments are formed on the same substrate, they can be arranged in any geometrical relation over the substrate. For example, in some embodiments of the present invention the sensing compartment is positioned at a region of the substrate which is separated from all the other compartments, and in some embodiments of the present invention the sensing compartment can be central while the other compartments are distributed to at least partially surround the sensing compartment.

System 300 preferably comprises a controller 30 configured for selectively operating each of valves 24 to control flow of fluids from compartment(s) 20 to compartment 12.

Controller 30 can include, or be associated with a data processor (not shown), which can be a general purpose computer or dedicated circuitry. Controller 30 preferably operates valves 24 automatically according to a predetermined sensing protocol which can be stored in the memory of the data processor.

In some embodiments of the present invention compartment 12 comprises an outlet port 36 from which fluids can exit compartment 12 (for example, following a washing operation). An outlet channel 38 can be connected to port 36 to facilitate the removal of fluids from compartment 12. The fluids can flow through port 36 into channel 38 by virtue of an overpressure generated in compartment 12 during the flow of fluids into compartment 12. The fluids can alternatively or additionally flow through port 36 into channel 38 by applying an under pressure (e.g., using a pump, not shown) in channel 38 as known in the art.

In some embodiments of the present invention, compartment 20 comprises an inlet port (not shown) for introducing e.g., a sample and/or a drug.

Exemplary Configurations:

In some embodiments, sensing system 100 is configured for use in vivo.

In some embodiments, system 300 is configured for use in vivo. In some embodiments, system 300 comprises one or more sensing compartment(s) 12 and one or more drug compartment(s) 20, is configured for use in vivo. In some of these embodiments, one or more of sensing compartment 12 and drug compartment 20 can be in a form of a microneedle or a plurality of microneedles.

Any configuration suitable for in vivo use is contemplated.

In exemplary embodiments, sensing system 100 or system 300 is configured as a skin patch.

In some embodiments, sensing system 100 or system 300 is configured for use ex vivo. In exemplary embodiments, sensing system 100 or system 300 is configured as a lab-on-chip system, as described herein.

In some of any of the embodiments described herein, the sensing system (e.g., sensing system 100) is devoid of a labeling agent (e.g. a chromophore, a fluorescent agent, a phosphorescent agent, a contrast agent, a radioactive agent, and the like).

In some embodiments, system 300 is devoid of a labeling agent.

The Manufacturing:

Embodiments of the present invention further relate to a process of preparing a sensing system as described herein.

In some embodiments, a sensing system as described herein is prepared by contacting a nanostructure featuring a polymerizable group on a surface thereof with a reaction mixture comprising a hydrogel precursor (hydrogel forming agent, or a mixture of hydrogel forming agents), a sensing moiety and an initiator, under conditions for effecting hydrogel formation. The reaction mixture is typically an aqueous solution comprising the hydrogel precursor, the sensing moiety and the initiator.

In some embodiments the process further comprises, prior to the contacting, generating a polymerizable group on a surface of the nanostructure. The surface polymerizable group can be generated by using a bifunctional reagent which comprises a reactive group for forming a covalent bond with intrinsic functional groups on the nanostructure surface and a polymerizable group, as described herein in the context of embodiments relating to the linker.

In some embodiments, the contacting is effected by depositing a hydrogel precursor solution on the nanostructure surface. The deposition can be effected, for example, by spin coating. Any other deposition methods are contemplated.

In some embodiments, the condition for effecting hydrogel formation may include, for example, a catalyst for initiating polymerization of the hydrogel precursor. A suitable catalyst can be selected according to the nature of the polymerizable and/or crosslinkable groups. For example, for polymerizable groups that polymerize by free radical polymerization, such as acrylate groups, a free radical initiator is used, optionally together with a co-catalyst. For polymerizable groups that polymerize via cationic polymerization, a cationic initiator is used. Suitable catalysts are well known to those skilled in the art.

In some embodiments, the condition for effecting hydrogel formation comprises exposure to electromagnetic radiation, for example, UV radiation. Alternatively, or in additional, the condition comprises exposure to heat energy.

The Sensing Method:

According to an aspect of some of any of the embodiments described herein, there is provided a method of detecting a target molecule. As used herein and in the art "detecting" encompasses determining a presence and/or amount of a target molecule (and analyte as described herein). The detecting can be used to monitor a presence and/or amount of a target molecule, if performed continuously or intermittently during a prolonged time period.

Any one of the sensing systems as described herein is usable for detecting a target molecule upon contacting the system with a sample containing the target molecule, as described herein.

When the sensing system forms a part of a microfluidic system as described herein, the contacting can be effected by contacting (e.g., introducing, by flowing, injecting, etc.) the sample compartment with the sample. Sensing can then be effected by controlling the fluid communication between each the sample compartment and the sensing compartment.

When two more types of nanostructures are employed (within the same or different sensing systems or compartments) sensing can be effected simultaneously, by contacting the sample with all nanostructures or all sensing systems at the same time. When the contacting is effected sequentially, washing one or more of the sensing compartment can be effected between sequential sensing.

In some embodiments, the system can further comprises a compartment (e.g., chamber) containing a washing fluid (e.g., washing solution). In some embodiments, a washing solution is used so as to "normalize" the hydrogel, namely, to remove analyte molecules or compounds generated upon interaction between the analyte and the sensing moiety or any other components present in the sample.

In some embodiments, the contacting is effected continuously, such that a sample is in continuous contact with the sensing system, and a presence and/or amount or level of the analyte in the sample is continuously monitored.

When a solution containing an analyte, optionally a physiological solution (e.g., a physiological medium), is contacted with a sensing system (directly or via a sample compartment as described herein) the signal generated by the sensing system is indicative for the presence and/or level of the analyte in the sample.

A reference data of signals generated by this method for various concentrations of various analytes can be used for processing data acquired from more complex samples, so as to monitor and analyze the level of the analyte, to thereby determine, for example, abnormal condition or an improvement thereof, as is discussed in further detail hereinafter.

In some embodiments, a sample is contacted per se with the sensing system.

Alternatively, a sample is first treated, for example, in a sample compartment, and is then contacted with the sensing system.

In an exemplary embodiment, a cell is introduced to a sample compartment (e.g., chamber), and subjected to culture conditions. For example, culture medium, which is stored in one chamber in the sample compartment is fluidly communicated with a chamber containing the cell. Thereafter, cultured cells are subjected, optionally, to viability assay, for determining number of viable cells and/or proliferation rate of the cells. For example, a portion of the cultured cells in the chamber can be fluidly communicated with another chamber, which includes conditions for a viability assay or proliferation assay. Alternatively or in addition, portion of the cultured cells can be subjected to another treatment, for example, by contacting a therapy or therapeutic agent (e.g., medicament or any other treatment), and be cultured in the presence of the medicament or treatment. Further alternatively, cells can first be cultured, and then subjected to a medicament or other treatment by being flowed to a chamber containing the medicament or treatment. Alternatively, cells can be flowed to another chamber and a solution containing the medicament or treatment can be introduced to a different chamber and be flowed to the same chamber as the cells.

In some of any one of the embodiments described herein for a method, after a chamber is fluidly communicating with a sensing compartment as described herein, one or more washing solutions, present in one or more chambers of the sample compartment, are fluidly communicated with the sensing compartment.

The Sample:

The sample contacted with any one of the sensing systems as described herein can be, for example, a solution containing the analyte, or, alternatively, a solution containing a substance the produces the analyte.

Alternatively, the sample is more complex and comprises, for example, cells, a biological sample, a biological sample comprising cells, each of which may further comprise additional agents, reagents, media and the like.

In some of any of the embodiments described herein, the sample comprises cells and the method can be used for determining a presence and/or amount of the analyte in the cells.

When the analyte is a metabolite, the method can be used for determining, monitoring and/or analyzing a metabolic activity of the cell.

As used herein "cell" refers to a prokaryotic or a eukaryotic cell for which the above metabolic activity can be measured. The cell can be a bacteria, yeast, plant, insect or mammalian cell. According to a specific embodiment, the cell is a human cell. It will be appreciated that the cell may refer to a single cell but may also refer to a plurality of cells. The cells may be isolated cells (having no tissue organization) or cells in a tissue or tissue fragment. According to a specific embodiment, when the cells are PBMCs, the assay is done on $10^3$-$10^{10}$ cells. According to a specific embodiment the number of cells is $10^6$-$10^7$.

The cell may be a differentiated cell, a non-differentiated cell (e.g., stem cell) or a dedifferentiated cell.

According to one embodiment, the cell is a cell of the immune system, that is a white blood cell (i.e., a leukocyte). Examples include, a neutrophil, an eosinophil, a basophil, a lymphocyte (T cell or B cell), a monocyte, a macrophage and a dendritic cell.

According to another embodiment, the cell is a pathogenic or diseased cell of any tissue such as a cancer cell. Other diseases and medical conditions which can be detected according to the present teachings are provided below.

Other cells which may be analyzed according to the present teachings include, but are not limited to, en embryonic cell (such as for IVF qualification), a red blood cell, a platelet, a bacterial-infected cell, a fungus-infected cell, and a viral infected cell.

Thus, the cell may refer to an isolated population of cells which comprise a highly purified subset of specific cells i.e., homogenic cell population (e.g. >80% purity), e.g., T cells, or a heterogenic cell population which comprises various types of immune cells such as peripheral blood leukocytes (PBL) or mononuclear cells.

Cells may be non-cultured, cultured primary cells or cloned cells (e.g., cell-line).

The cells may be adherent cells or cells in suspension.

According to further embodiments, the cells can be non-genetically modified or genetically modified.

According to some of any of the embodiments described herein, two or more samples, each comprising a different cell or a different solution of a cell, can be introduced simultaneously to the system (e.g., each sample is introduced to a different chamber in a sample compartment). Optionally, introducing is without pre-processing the sample.

Each of these samples can be subjected to the same or different treatments before sensing is effected, as described herein.

Optionally, the same sample is subjected to different treatments, and sensing is effected upon each subjection.

A sample as described herein can be a cellular biological sample.

Exemplary cellular biological samples include, but are not limited to, blood (e.g., peripheral blood leukocytes, peripheral blood mononuclear cells, whole blood, cord blood), a solid tissue biopsy, cerebrospinal fluid, urine, lymph fluids, and various external secretions of the respiratory, intestinal and genitourinary tracts, synovial fluid, amniotic fluid and chorionic villi.

Biopsies include, but are not limited to, surgical biopsies including incisional or excisional biopsy, fine needle aspirates and the like, complete resections or body fluids. Methods of biopsy retrieval are well known in the art.

Upon being contacted with the system, cells in any one of the samples described herein can be grown within the chamber to which they are introduced, either in physiological medium or in the presence of additional reagents (e.g., a medicament, as described herein).

In some embodiments, the sample is a physiological sample, drawn from a subject, for example, a cellular biological sample as described herein. In these embodiments, detecting the analyte (a bioanalyte) is effected ex vivo.

In some embodiments, the sample is a tissue or an organ of a subject, and detecting the analyte (a bioanalyte) is effected in vivo.

In these embodiments, a sensing system as described herein, or a microfluidic system containing the sensing system as described herein is configured so as to contact the tissue or organ of the subject. In exemplary embodiments, the sensing system or a system comprising the sensing system is configured as a skin patch, and a tissue of the subject (e.g., blood tissue) is contacted with the sensing system by means of, for example, microneedles. Any other configurations that allow contacting an organ or a tissue of subject in vivo are contemplated.

Applications:

The sensing system of the present embodiments can be used in many applications, including without limitation, chemical applications, genetic applications, biochemical applications, pharmaceutical applications, biomedical applications, medical applications, radiological applications and environmental applications.

The sensing can thus be selected such that a detectable change occurs once the target molecule contacts the sensing compartment.

For medical applications, the sensing system of the present embodiments is suitable for diagnostic and patient management, as is described and exemplified hereinafter. For environmental applications the sensing system of the present embodiments is suitable for detecting hazardous materials or conditions such as air or water pollutants, chemical agents, biological organisms or radiological conditions. For genetic and biochemical applications the sensing system of the present embodiments is suitable for testing and/or analysis of DNA, and other macro or smaller molecules, or reactions between such molecules in an approach known as "lab-on-chip."

The sensing system of the present embodiments can also be used in the area of biochemical and biophysical investigations of single cells. For example, the sensing system can isolate a cell or a group of cells of a certain type.

The system and method of the present embodiments can be used for sensing presence of target molecules in many types of fluid media and objects present in fluid media. The objects can comprise organic, inorganic, biological, polymeric or any other material. For example, the fluid medium can comprise blood product, either whole blood or blood component, in which case the objects can be erythrocytes, leukocytes, platelets and the like. The fluid medium can also comprise other body fluids, including, without limitation, saliva, cerebral spinal fluid, urine and the like. Also contemplated are various buffers and solutions, such as, but not limited to, nucleic acid solutions, protein solutions, peptide solutions, antibody solutions and the like. Also contemplated are various biological and chemical reagents such as, but not limited to, oxidizing agents, reducing agents, enzymes, receptor ligands, extracellular components, metabolites, fatty acids, steroids, and the like.

Objects in the fluid medium can comprise other materials, such as, but not limited to, cells, bacteria, cell organelles, platelets, macromolecules, vesicles, microbeads, covered with antibodies specific to soluble factors such as ligands, shaded receptors and biological materials containing a fatty tissue or a microorganism. The objects which are manipulated by the system and method of the present embodiments can also be made of or comprise synthetic (polymeric or non-polymeric) material, such as latex, silicon polyamide and the like. The object can be optically visible or transparent. The objects can also emit light or be conjugated to other objects to facilitate their detection.

A sensing method as described hereinabove, can be utilized in a variety of diagnostic and therapeutic applications.

In some embodiments, a sample which comprises a cell further comprises a therapeutic agent, and the method as described herein is used for determining or monitoring activity of the cell upon contacting the therapeutic agent.

Such a method can be used for determining an efficacy of the therapeutic agent towards the cell.

In some embodiments the analyte is a metabolite, and the method is being for monitoring a metabolic activity (MA) of a cell.

According to an aspect of some embodiments of the present invention, there is provided a method of monitoring a metabolic activity of a cell. The method is effected contacting the cell with any one of the sensing systems as described herein.

In some embodiments of this aspect, a cell can be connected with a microfluidic system as described herein, cultured, and then, portions of the cultured cells can be fluidly communicated with a suitable sensing compartment, as described herein.

A method of monitoring a metabolic activity of a cell can be used, for example, for identifying an agent capable of altering a metabolic activity of the cell, wherein cells cultured, for example, in a system as described herein, are subjected to a condition which includes a tested agent, and then metabolic activity is determined as described herein. Cultured cells can be subjected simultaneously to different agents, in different chambers, and each of these chambers can then be subjected to sensing, as described herein.

Using as the sample a biological sample as described herein of a subject in any of the embodiments of a method as described herein can be used for diagnosing a disease associated with a metabolic activity in the subject.

Alternatively, such a method can be used for monitoring a treatment of a disease associated with a modified metabolic activity in the subject.

In some embodiments, the method comprises contacting at least two samples with the sensing system, and the method is being for simultaneously or sequentially determining a presence and/or an amount of the analyte in the at least two samples. In one exemplary embodiment, the two samples include cells, one healthy cells and one diseased cells, and the method allows comparing the change in metabolic activity of a diseased cell. In one exemplary embodiment, the two samples include diseased cells, one subjected to a therapeutic condition (e.g., medicament or treatment) and one subjected to another therapeutic condition or is not subjected to any condition, and the method allows comparing a change in metabolic activity of a diseased cell as a result of the therapeutic condition, and thus is indicative of a therapeutic efficacy of the tested therapeutic agent.

According to an aspect of some embodiments of the present invention there is provided a method of diagnosing a disease associated with a modified metabolic activity in a subject in need thereof. The method is effected by contacting a cellular sample (a biological cellular sample as described herein) of the subject with a sensing system as described herein, and determining a presence and/or amount of one or more metabolites in the sample, as described herein.

The subject may be a healthy animal or a human subject undergoing a routine well-being check up. Alternatively, the subject may be at risk of having a disease associated with a modified metabolic activity such as cancer (e.g., a genetically predisposed subject, a subject with medical and/or family history of cancer, a subject who has been exposed to carcinogens, occupational hazard, environmental hazard) and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness).

As used herein the term "diagnosis" or "diagnosing" refers to determining presence or absence of a pathology (e.g., a disease, disorder, condition or syndrome), classifying a pathology or a symptom, determining a severity of the pathology, monitoring pathology progression, forecasting an outcome of a pathology and/or prospects of recovery and screening of a subject for a specific disease.

As used herein "a disease associated with a modified metabolic activity" refers to a disease that is characterized by a cell population that has undergone a shift in metabolic activity as compared to an identical cell population taken from a normal, healthy (unaffected with the disease). That cell population that has undergone a shift in metabolic activity, can be a pathogenic cell population (i.e., disease-causing cells e.g., cancer cells) or a non-pathogenic cell population (e.g., disease combating cells e.g., immune cells such as in the case of solid-tumor). For instance, in oncology, most cancer cells predominantly and some populations of the immune system undergoing clonal expansion produce energy by a high rate of glycolysis followed by lactic acid production in the cytosol, rather than by a comparatively low rate of glycolysis followed by oxidation of pyruvate in mitochondria like most normal cells.

According to some embodiments, the level (presence and/or amount) of one or more metabolite(s) in a normal, healthy (unaffected) sample of identical cell composition are determined under identical conditions which were used to monitor the cells of the subject.

A shift (i.e., a change) in the metabolic activity (a level of one or more metabolites) between the cells of the subject and those of the control (normal, unaffected), as evidenced from the metabolites level(s) obtained under identical conditions, is indicative of a disease associated with the modified metabolic activity profiles.

Thus, for example, data acquired by a method as described herein for level (amount) of metabolites like lactate, optionally combined with data for level of glucose and/or pyruvate, can be compared with data presenting levels of one or more of these metabolites in normal cells, so as to determine is a subject has cancer. Moreover, such data can be compared with other data for more accurately determine a type of cancer and/or its origin and/or its stage, based on the level of one or more of these metabolites in the biological cellular sample.

The results of the metabolic activity assay may be subject to decision tree models which classify the results and assist in final diagnosis. According to a preferred embodiment, at least two models are combined. Examples of such models include, but are not limited to, CHAID, C5 and C&R Tree. The Logistic model may be further applied.

Similarly to metabolites, determining a presence and/or amount of other biomarkers can be used for determining abnormal activity in a cellular biological sample. For example, the method can be used for detecting of overexpression of receptors that is associated with a disease, or for detecting a presence and/or amount of biomarkers such as antigens which are indicative of a disease.

Examples of medical conditions which can be diagnosed and treated (as is further described hereinbelow) according to the present teachings include, but are not limited to, cancer, pathogenic infection and autoimmune diseases. Specific examples are provided in the following.

Inflammatory diseases include, but are not limited to, chronic inflammatory diseases and acute inflammatory diseases.

Inflammatory diseases associated with hypersensitivity diseases associated with hypersensitivity such as, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH. Included are the following, as non-limiting examples:

Type I or immediate hypersensitivity, such as asthma;

Type II hypersensitivity such as, but are not limited to, rheumatoid diseases, rheumatoid autoimmune diseases, rheumatoid arthritis, spondylitis, ankylosing spondylitis, systemic diseases, systemic autoimmune diseases, systemic lupus erythematosus, sclerosis, systemic sclerosis, glandular diseases, glandular autoimmune diseases, pancreatic autoimmune diseases, diabetes, Type I diabetes, thyroid diseases, autoimmune thyroid diseases, Graves' disease, thyroiditis, spontaneous autoimmune thyroiditis, Hashimoto's thyroiditis, myxedema, idiopathic myxedema; autoimmune reproductive diseases, ovarian diseases, ovarian autoimmunity, autoimmune anti-sperm infertility, repeated fetal loss, neurodegenerative diseases, neurological diseases, neurological autoimmune diseases, multiple sclerosis, Alzheimer's disease, myasthenia gravis, motor neuropathies, Guillain-Barre syndrome, neuropathies and autoimmune neuropathies, myasthenic diseases, Lambert-Eaton myasthenic syndrome, paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies; neuropathies, dysimmune neuropathies; neuromyotonia, acquired neuromyotonia, arthrogryposis multiplex congenita, cardiovascular diseases, cardiovascular autoimmune diseases, atherosclerosis, myocardial infarction, thrombosis, granulomatosis, Wegener's granulomatosis, arteritis, Takayasu's arteritis and Kawasaki syndrome; anti-factor VIII autoimmune disease; vasculitises, necrotizing small vessel vasculitises, microscopic polyangiitis, Churg and Strauss syndrome, glomerulonephritis, pauci-immune focal necrotizing glomerulonephritis, crescentic glomerulonephritis; antiphospholipid syndrome; heart failure, agonist-like β-adrenoceptor antibodies in heart failure, thrombocytopenic purpura; hemolytic anemia, autoimmune hemolytic anemia, gastrointestinal diseases, autoimmune diseases of the gastrointestinal tract, intestinal diseases, chronic inflammatory intestinal disease, celiac disease, autoimmune diseases of the musculature, myositis, autoimmune myositis, Sjogren's syndrome; smooth muscle autoimmune disease, hepatic diseases, hepatic autoimmune diseases, autoimmune hepatitis and primary biliary cirrhosis.

Type IV or T cell mediated hypersensitivity, include, but are not limited to, rheumatoid diseases, rheumatoid arthritis, systemic diseases, systemic autoimmune diseases, systemic lupus erythematosus, glandular diseases, glandular autoimmune diseases, pancreatic diseases, pancreatic autoimmune diseases, Type 1 diabetes; thyroid diseases, autoimmune thyroid diseases, Graves' disease; ovarian diseases, prostatitis, autoimmune prostatitis, polyglandular syndrome, autoimmune polyglandular syndrome, Type I autoimmune polyglandular syndrome, neurological diseases, autoimmune neurological diseases, multiple sclerosis, neuritis, optic neuritis, myasthenia gravis, stiff-man syndrome, cardiovascular diseases, cardiac autoimmunity in Chagas' disease, autoimmune thrombocytopenic purpura, anti-helper T lymphocyte autoimmunity, hemolytic anemia, hepatic diseases, hepatic autoimmune diseases, hepatitis, chronic active hepatitis, biliary cirrhosis, primary biliary cirrhosis, nephric diseases, nephric autoimmune diseases, nephritis, interstitial nephritis, connective tissue diseases, ear diseases, autoimmune connective tissue diseases, autoimmune ear disease, disease of the inner ear, skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune diseases such as, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing and crescentic glomerulonephritis, antiphospholipid syndrome, antibody-induced heart failure, thrombocytopenic purpura, autoimmune hemolytic anemia, cardiac autoimmunity in Chagas' disease and anti-helper T lymphocyte autoimmunity.

Examples of autoimmune rheumatoid diseases include, but are not limited to rheumatoid arthritis and ankylosing spondylitis.

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes, autoimmune thyroid diseases, Graves' disease, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Examples of autoimmune gastrointestinal diseases include, but are not limited to, chronic inflammatory intestinal diseases, celiac disease, colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis, primary biliary cirrhosis and autoimmune hepatitis.

Examples of autoimmune neurological diseases include, but are not limited to, multiple sclerosis, Alzheimer's disease, myasthenia gravis, neuropathies, motor neuropathies; Guillain-Barre syndrome and autoimmune neuropathies, myasthenia, Lambert-Eaton myasthenic syndrome; paraneoplastic neurological diseases, cerebellar atrophy, paraneoplastic cerebellar atrophy and stiff-man syndrome; non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies; dysimmune neuropathies; acquired neuromyotonia, arthrogryposis multiplex congenita, neuritis, optic neuritis and neurodegenerative diseases.

Examples of autoimmune muscular diseases include, but are not limited to, myositis, autoimmune myositis and primary Sjogren's syndrome and smooth muscle autoimmune disease.

Examples of autoimmune nephric diseases include, but are not limited to, nephritis and autoimmune interstitial nephritis.

Examples of autoimmune diseases related to reproduction include, but are not limited to, repeated fetal loss.

Examples of autoimmune connective tissue diseases include, but are not limited to, ear diseases, autoimmune ear diseases and autoimmune diseases of the inner ear.

Examples of autoimmune systemic diseases include, but are not limited to, systemic lupus erythematosus and systemic sclerosis.

Infectious diseases such as, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases.

Graft rejection diseases including diseases associated with transplantation of a graft such as, but are not limited to, graft rejection, chronic graft rejection, subacute graft rejection, hyperacute graft rejection, acute graft rejection and graft versus host disease.

Allergic diseases which include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a specific embodiment the disease is cancer.

Cancerous diseases include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, paccreas, cervix, prostate, and ovarian.

Thus, the present teachings can be used in disease detection. Following is a non-limiting embodiment which relates to early cancer detection.

Disease diagnosis made according to the present teachings is followed by substantiation of the screen results using gold standard methods. Once diagnosis is established either relying on the present teachings or substantiated using Gold standard methods, the subject is informed of the diagnosis and treated as needed.

Thus, according to an aspect of some embodiments of the invention there is provided a method of disease treatment in a subject in need thereof, the method comprising:

(a) diagnosing a presence of the disease in the subject according to the method described above; and
(b) treating the subject based on the diagnosis.

Embodiments of the present invention have a variety of applications pertaining to individually optimizing disease treatment, monitoring disease treatment in a subject, determining a treatment for a subject and identifying an agent capable of treating a disease in a subject.

According to an aspect of some embodiments of the invention there is provided a method of individually optimizing disease treatment, the method comprising:

determining a presence and/or amount of a bioanalyte in a biological sample of the subject which comprises a cell with at least one medicament, using any one of the relevant methods as described herein, including any embodiments thereof, whereas a shift in the level of the bioanalyte in the cell towards that of a normal healthy cell sample examined under identical conditions is indicative of an efficacious medicament for the disease.

As used herein "individually optimizing treatment" refers to an ex vivo method of tailoring treatment regimen (e.g., type of medicament, dose).

As used herein a "medicament" describes a formulation of a medicine, medicinal drug or medication, as interchangeably used herein. Examples of medicaments, include but are not limited to, chemotherapy, antibiotics, antiparasitic drugs, antiviral and the like.

As used herein throughout, for any of the relevant embodiments described herein, a "therapy" describes a therapeutic agent, which is also referred to herein as a medicament, as well as other treatments such as, for example, radiation, dehydration, devitalization, and the like.

Cells of a biological sample can be contacted with a medicament or any other treatment within a sample compartment of a system, as described herein.

In the context of these embodiments, the term "contacting" refers to bringing the medicament into the vicinity of a cell under conditions such that the medicament contacts the cell membrane and if needed internalizes thereto. Thus, for example, the contacting should be effected under buffer conditions, at a temperature and time sufficient to allow the medicament to affect cell phenotype (e.g., cytotoxic or cytostatic effect). The contacting may be effected in vitro, ex vivo or in vivo.

According to a specific embodiment, "a shift in the level of an analyte in the cell towards that of a normal healthy cell sample examined under identical conditions" refers to at least a 10% local or global (throughout the profile) shift preferably towards 100% identity to the control normal healthy cell sample.

A shift beyond a predetermined threshold as will be determined by the skilled artisan as indicative of an efficacious treatment.

According to an aspect of some embodiments of the present invention there is provided a method of monitoring disease treatment in a subject, the method comprising:

(a) administering at least one medicament against the disease to the subject; and
(b) determining a level of one or more bioanalytes in the sample,
wherein a shift in the level of the one or more bioanalytes in the sample towards that of a normal healthy sample examined under identical conditions is indicative of an efficacious treatment of the disease.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" in the context of abnormal activity, disease or condition, includes abrogating, substantially inhibiting, slowing or reversing the progression of a condition, substantially ameliorating clinical or aesthetical symptoms of a condition or substantially preventing the appearance of clinical or aesthetical symptoms of a condition.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group" it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. A hydrocarbon can be a linking group or an end group.

As used herein, the term "amine" describes both a —NRxRy group and a —NRx-group, wherein Rx and Ry are each independently hydrogen, alkyl, cycloalkyl, aryl, as these terms are defined hereinbelow.

The amine group can therefore be a primary amine, where both Rx and Ry are hydrogen, a secondary amine, where Rx is hydrogen and Ry is alkyl, cycloalkyl or aryl, or a tertiary amine, where each of Rx and Ry is independently alkyl, cycloalkyl or aryl.

Alternatively, Rx and Ry can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NRxRy group in cases where the amine is an end group, as defined hereinunder, and is used herein to describe a —NRx-group in cases where the amine is a linking group or is or part of a linking moiety.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms (C(1-4) alkyl). The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene and alkyne, as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofuran, tetrahydropyrane, morpholino, oxalidine, and the like. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof. The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "halide" and "halo" describes fluorine, chlorine, bromine or iodine.

The term "haloalkyl" describes an alkyl group as defined above, further substituted by one or more halide.

The term "sulfate" describes a —O—S($=$O)$_2$—ORx end group, as this term is defined hereinabove, or an —O—S($=$O)$_2$—O— linking group, as these phrases are defined hereinabove, where Rx is as defined hereinabove.

The term "thiosulfate" describes a —O—S($=$S)($=$O)—ORx end group or a —O—S($=$S)($=$O)—O— linking group, as these phrases are defined hereinabove, where Rx is as defined hereinabove.

The term "sulfite" describes an —O—S($=$O)—O— Rx end group or a —O—S($=$O)—O— group linking group, as these phrases are defined hereinabove, where Rx' is as defined hereinabove.

The term "thiosulfite" describes a —O—S($=$S)—O—Rx end group or an —O—S($=$S)—O— group linking group, as these phrases are defined hereinabove, where Rx is as defined hereinabove.

The term "sulfinate" describes a —S($=$O)—ORx end group or an —S($=$O)—O— group linking group, as these phrases are defined hereinabove, where Rx is as defined hereinabove.

The term "sulfoxide" or "sulfinyl" describes a —S($=$O)Rx end group or an —S($=$O)— linking group, as these phrases are defined hereinabove, where Rx is as defined hereinabove.

The term "sulfonate" describes a —S($=$O)$_2$—Rx end group or an —S($=$O)$_2$— linking group, as these phrases are defined hereinabove, where Rx is as defined herein.

The term "S-sulfonamide" describes a —S($=$O)$_2$—NRxRy end group or a —S($=$O)$_2$—NRx- linking group, as these phrases are defined hereinabove, with Rx and Ry as defined herein.

The term "N-sulfonamide" describes an RxS($=$O)$_2$—NRy— end group or a —S($=$O)$_2$—NRx— linking group, as these phrases are defined hereinabove, where Rx and Ry are as defined herein.

The term "disulfide" refers to a —S—SRx end group or a —S—S— linking group, as these phrases are defined hereinabove, where Rx is as defined herein.

The term "phosphonate" describes a —P($=$O)(ORx)(ORy) end group or a —P($=$O)(ORx)(O)— linking group, as these phrases are defined hereinabove, with Rx and Ry as defined herein.

The term "thiophosphonate" describes a —P($=$S)(ORx)(ORy) end group or a —P($=$S)(ORx)(O)— linking group, as these phrases are defined hereinabove, with Rx and Ry as defined herein.

The term "phosphinyl" describes a —PRxRy end group or a —PRx— linking group, as these phrases are defined hereinabove, with Rx and Ry as defined hereinabove.

The term "phosphine oxide" describes a —P($=$O)(Rx)(Ry) end group or a —P($=$O)(Rx)— linking group, as these phrases are defined hereinabove, with Rx and Ry as defined herein.

The term "phosphine sulfide" describes a —P($=$S)(Rx)(Ry) end group or a —P($=$S)(Rx)— linking group, as these phrases are defined hereinabove, with Rx and Ry as defined herein.

The term "phosphite" describes an —O—PRx($=$O)(ORy) end group or an —O—PRx($=$O)(O)— linking group, as these phrases are defined hereinabove, with Rx and Ry as defined herein.

The term "carbonyl" or "carbonate" as used herein, describes a —C($=$O)—Rx end group or a —C($=$O)— linking group, as these phrases are defined hereinabove, with Rx as defined herein.

The term "thiocarbonyl" as used herein, describes a —C($=$S)—Rx end group or a —C($=$S)— linking group, as these phrases are defined hereinabove, with Rx as defined herein.

The term "oxo" as used herein, describes a ($=$O) group, wherein an oxygen atom is linked by a double bond to the atom (e.g., carbon atom) at the indicated position.

The term "thiooxo" as used herein, describes a ($=$S) group, wherein a sulfur atom is linked by a double bond to the atom (e.g., carbon atom) at the indicated position.

The term "oxime" describes a $=$N—OH end group or a $=$N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "isocyanate" describes an —N$=$C$=$O group.

The term "isothiocyanate" describes an —N=C=S group.

The term "nitro" describes an —NO$_2$ group.

The term "acyl halide" describes a —(C=O)Rz group wherein Rz is halide, as defined hereinabove.

The term "azo" or "diazo" describes an —N=NRx end group or an —N=N— linking group, as these phrases are defined hereinabove, with Rx as defined hereinabove.

The term "peroxo" describes an —O—ORx end group or an —O—O— linking group, as these phrases are defined hereinabove, with Rx as defined hereinabove.

The term "carboxylate" as used herein encompasses C-carboxylate and O-carboxylate.

The term "C-carboxylate" describes a —C(=O)—ORx end group or a —C(=O)—O— linking group, as these phrases are defined hereinabove, where Rx is as defined herein.

The term "O-carboxylate" describes a —OC(=O)Rx end group or a —OC(=O)— linking group, as these phrases are defined hereinabove, where Rx is as defined herein.

A carboxylate can be linear or cyclic. When cyclic, Rx and the carbon atom are linked together to form a ring, in C-carboxylate, and this group is also referred to as lactone. Alternatively, Rx and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—ORx end group or a —C(=S)—O— linking group, as these phrases are defined hereinabove, where Rx is as defined herein.

The term "O-thiocarboxylate" describes a —OC(=S)Rx end group or a —OC(=S)— linking group, as these phrases are defined hereinabove, where Rx is as defined herein.

A thiocarboxylate can be linear or cyclic. When cyclic, Rx and the carbon atom are linked together to form a ring, in C-thiocarboxylate, and this group is also referred to as thiolactone. Alternatively, Rx and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an RyOC(=O)—NRx— end group or a —OC(=O)—NRx— linking group, as these phrases are defined hereinabove, with Rx and Ry as defined herein.

The term "O-carbamate" describes an —OC(=O)—NRxRy end group or an —OC(=O)—NRx— linking group, as these phrases are defined hereinabove, with Rx and Ry as defined herein.

A carbamate can be linear or cyclic. When cyclic, Rx and the carbon atom are linked together to form a ring, in O-carbamate. Alternatively, Rx and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NRxRy end group or a —OC(=S)—NRx— linking group, as these phrases are defined hereinabove, with Rx and Ry as defined herein.

The term "N-thiocarbamate" describes an RyOC(=S)NRx— end group or a —OC(=S)NRx— linking group, as these phrases are defined hereinabove, with Rx and Ry as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NRxRy end group or a —SC(=S)NRx—linking group, as these phrases are defined hereinabove, with Rx and Ry as defined herein.

The term "N-dithiocarbamate" describes an RySC(=S)NRx—end group or a —SC(=S)NRx— linking group, as these phrases are defined hereinabove, with Rx and Ry as defined herein.

The term "urea", which is also referred to herein as "ureido", describes a —NRxC(=O)—NRyRq end group or a —NRxC(=O)—NRy— linking group, as these phrases are defined hereinabove, where Rz and Ry are as defined herein and Rq is as defined herein for Rx and Ry.

The term "thiourea", which is also referred to herein as "thioureido", describes a —NRx-C(=S)—NRyRq end group or a —NRx-C(=S)—NRy— linking group, with Rx, Ry and Rq as defined herein.

The term "amide" as used herein encompasses C-amide and N-amide.

The term "C-amide" describes a —C(=O)—NRxRy end group or a —C(=O)—NRx— linking group, as these phrases are defined hereinabove, where Rx and Ry are as defined herein.

The term "N-amide" describes a RxC(=O)—NRy— end group or a RxC(=O)—N— linking group, as these phrases are defined hereinabove, where Rx and Ry are as defined herein.

An amide can be linear or cyclic. When cyclic, Rx and the carbon atom are linked together to form a ring, in C-amide, and this group is also referred to as lactam. Cyclic amides can function as a linking group, for example, when an atom in the formed ring is linked to another group.

The term "guanyl" describes a RxRyNC(=N)— end group or a —RxNC(=N)— linking group, as these phrases are defined hereinabove, where Rx and Ry are as defined herein.

The term "guanidine" describes a —RxNC(=N)—NRyRq end group or a —RxNC(=N)—NRy— linking group, as these phrases are defined hereinabove, where Rx, Ry and Rq are as defined herein.

The term "hydrazine" describes a —NRx-NRyRq end group or a —NRx-NRy— linking group, as these phrases are defined hereinabove, with Rx, Ry, and Rq as defined herein.

As used herein, the term "hydrazide" describes a —C(=O)—NRx-NRyRq end group or a —C(=O)—NRx-NRy— linking group, as these phrases are defined hereinabove, where Rx, Ry and Rq are as defined herein.

As used herein, the term "thiohydrazide" describes a —C(=S)—NRx-NRyRq end group or a —C(=S)—NRx-NRy— linking group, as these phrases are defined hereinabove, where Rx, Ry and Rq are as defined herein.

As used herein, the term "alkylene glycol" describes a —O—[(CRxRy)$_z$-O]$_y$Rq end group or a —O—[(CRxRy)$_z$-O]$_y$— linking group, with Rx, Ry and Rq being as defined herein, and with z being an integer of from 1 to 10, preferably, 2-6, more preferably 2 or 3, and y being an integer of 1 or more. Preferably Rx and Ry are both hydrogen. When z is 2 and y is 1, this group is ethylene glycol. When z is 3 and y is 1, this group is propylene glycol.

When y is greater than 4, the alkylene glycol is referred to herein as poly(alkylene glycol). In some embodiments of the present invention, a poly(alkylene glycol) group or moiety can have from 10 to 200 repeating alkylene glycol units, such that z is 10 to 200, preferably 10-100, more preferably 10-50.

The terms "acrylate", "methacrylate", "acrylamide" and methacrylamide" can be collectively represented by the following Formula:

Formula II wherein when $R_1$ is a carboxylate, and the compound is an acrylate or methacrylate, and when R1 is amide, the compound is an acrylamide or methacrylamide. When $R_2$ is methyl, and the compound is methacrylate o methacrylamide.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Fabrication of SiNW-FET

SiNW-FET was fabricated according to Patolsky et al., Nat Protoc. 2006; 1(4):1711-24. 20 nm diameter P-type SiNW-FET devices were fabricated by photolithography on 3 inch silicon wafer with 600 nm oxide layer.

Briefly, source and drain electrodes were deposited with the use of a multilayer photoresist structure consisting of 500 nm LOR5A (Microchem) and 500 nm 1805 (Shipley). After exposure and development of the electrode patterns, the contacts were metallized by e-beam and thermal evaporation of Ni (60 nm) respectively, and were then passivated with an insulating layer of $Si_3N_4$ (60 nm thick) deposited by plasma-enhanced chemical vapor deposition at 80° C. (ICP-PECVD, Axic Inc.) and a layer of 10 nm alumina (ALD deposition using a Cambridge Nanotech Savannah 200 system). The separation between the source and drain electrodes for each FET was 2 μm.

The process is schematically illustrated in FIG. 2B, and the SiNW-FET system is schematically illustrated in FIG. 2A.

The fabrication of the fluid-delivery device from flexible polydimethylsiloxane (PDMS) elastomer was performed according to Patolsky et al., Nat Protoc. 2006; 1(4):1711-24, with the following modifications: The PDMS was incubated with curing agent at 10:1 mass ratio for overnight at 60° C. The resulting device was then cut into rectangular pieces, at dimensions of 10×10×5 mm. Upstream polyethylene tube (PE 20, Intramedic) was 14 cm long and had 0.38 mm inner diameter. Downstream Tygon tube (S-50-HL, Tygon) was 13 cm long.

Example 2

Preparation of SiNW-FET Modified by Covalent Attachment of a Hydrogel Having a Sensing Moiety Impregnated Therein A modification of silicon nanowires (SiNW) FET system so as to immobilize thereto GOx-impregnated hydrogels is schematically illustrated in FIG. 3. The process is briefly described as follows:

A SiNW FET prepared as described in Example 1 herein was activated by oxygen plasma treatment (15 minutes, 100 W, 0.400 Torr).

The SiNWs were then treated for 60 minutes, at room temperature, with a 1 mM solution of 3-(Trichlorosilyl) propyl methacrylate (TPM) in a mixture of heptane and carbon tetrachloride 4:1 ratio, in a glove box under argon atmosphere, and were thereafter washed with hexane and isopropanol, in accordance with a procedure described in Revzin et al., Langmuir, 2001, 17, 5440-5447. The resulting modified SiNWs feature surface acrylate groups.

Attachment of a hydrogel to the SiNWs surface was performed similar to a procedure described in Piao et al., Biosensors and Bioelectronics 65 (2015) 220-225. A stock solution of poly(ethylene glycol) diacrylate (PEG-DA, MW 575) and 1 wt. % of 2-hydroxy-2-methylpropiophenone (HMPP) initiator was prepared and stored at 4° C. until used. A hydrogel precursor solution comprising of 67 vol. % of PEG-DA stock solution and 3.33 mg/mL glucose oxidase (GOx) in a Tris buffer (pH 7.4) was prepared and deposited on the acrylate-modified SiNW FET by means of spin coating, using spin coater (WS-400B-6NPP/LITE/10K, Laurell Technologies Corporation.), and exposed to UV light (320-380 nm filter), so as to form GOx-impregnating hydrogel film on the surface of the SiNWs. The remaining hydrogel precursor solution was flushed by a phosphate buffered saline (150 mM, pH 7.4).

The resulting modified SiNW FET system features a poly(ethylene glycol)diacrylate hydrogel covalently attached to the SiNWs surface and impregnating GOx therein.

Hydrogels impregnating other sensing moieties are similarly prepared by replacing GOx with a desired sensing moiety that selectively interacts with a target analyte and/or using other hydrogel precursor moieties.

Hydrogels impregnating other moieties, for example, non-sensing moieties, are similarly prepared by replacing GOx with a moiety of choice.

Non-impregnated hydrogels are also similarly prepared, by spin coating a hydrogel precursor solution without a sensing moiety.

FIG. 4 presents a scanning electron microscope image, taken using Quanta 200 FEG environmental scanning electron microscope (5 KV, secondary electron imaging), of source and drain electrodes of a silicon nanowire device having a GOx-impregnating hydrogel film attached thereto. Shown in the inset are data obtained in profilometer measurements, taken using Profilometer Dektak® 8 Veeco, of the GOx-impregnating hydrogel film on the device, and presenting the thickness of the hydrogel (the height of the hydrogel compared to the silicon wafer surface).

Example 3

Sensing

The modified SiNW FET system of Example 2 is utilized for sensing various bioanalytes, by selecting a sensing moiety that selectively interacts with the target analyte. The introduction of the analyte to the hydrogel (e.g., by contacting a sample containing the analyte with the SiNW FET system causes a specific deformation of the hydrogel matrix and this deformation leads to changes in the charge distribution (e.g., charge density) on the nanowires' surface and alter the conductivity of the system. The change is conductivity is readily detectable and is indicative at least of the presence of the analyte in the sample.

In an exemplary assay, sensing of glucose, as an exemplary metabolite, was performed by using a GOx-impregnated hydrogel immobilized to a SiNW FET system as described in Example 2, by applying the following parameters: $V_{Source\text{-}Drain}$=0.4 Volt, $V_{gate}$=−0.5 Volt, PDMS channel, 20 µl/min flow rate.

FIG. 5 presents an illustration of an exemplary sensing of glucose by a GOx-impregnated hydrogel immobilized to a SiNW FET system as described in Example 2. As a result of an increase of the conductivity of the SiNWs upon introduction of glucose to the system, the current in the SiNW FET system is increased.

FIG. 6 presents another illustration of an exemplary sensing of an antigen by an antibody-impregnated hydrogel immobilized to a SiNW FET system as described in Example 2. As a result of an increase of the conductivity of the SiNWs upon introduction of the respective antigen to the system, the current in the SiNW FET system is increased.

In another exemplary assay, detection of glucose using a GOx-impregnated hydrogel immobilized to a SiNW FET system as described in Example 2 was performed with a solution of glucose, at various concentrations, in 155 mM phosphate-buffered saline (PBS), using gate voltage of −0.5 volt and source-drain voltage of 0.4 volt. The samples were introduced to the system via a PDMS channel at constant flow rate of 20 µl/min. A constant gate voltage (Vg=−0.5 volt) was applied during the whole experiment. A constant source drain voltage (Vsd=0.4 volt) was applied during the whole experiment, except during samples exchange in which the source drain voltage was off (Vsd=0 volt), as illustrated in FIG. 7A between times 150-250 seconds, 550-680 and 1100-1200, and in FIG. 7B between times 0-100 seconds and 600-780. FIG. 7A illustrates the signals that were obtained from the introduction of samples to GOx-impregnated hydrogel SiNW FET device according to the following order: at 0-150 seconds the device was washed with PBS (Vsd=0.4, Vg=−0.5), at 250-550 seconds the device was washed with 1 mM glucose in PBS (Vsd=0.4, Vg=−0.5), at 680-1100 seconds the device was washed with 10 mM glucose in PBS (Vsd=0.4, Vg=−0.5). FIG. 7B illustrates the signals that were obtained from the introduction of samples to GOx-impregnated hydrogel SiNW FET device according to the following order: at 100-600 seconds the device was washed with 10 mM pyruvate in PBS (Vsd=0.4, Vg=−0.5), at 800-1500 seconds the device was washed with PBS only (Vsd=0.4, Vg=−0.5).

Data showing a normalized signal as a function of time was collected, and is presented in FIG. 7A. In the graph shown in FIG. 7A, at 0-150 seconds is presented a signal obtained from PBS only, at 250-550 seconds is presented a signal obtained from 1 mM glucose in PBS, and at 680-1100 seconds is presented a signal obtained from 10 mM glucose in PBS.

In the inset of FIG. 7A, an image of the nanowire chip system used in this assay, comprising 200 nanowires on a printed circuit board, and having immobilized on its surface a GOx-impregnating hydrogel film (marked in red) is presented.

The same assay was performed with a solution containing pyruvate in PBS, and the obtained data is presented in FIG. 7B. As shown therein, the GOx-impregnated hydrogel exhibits no response to pyruvate, indicating its selective response to glucose. In the graph shown in FIG. 7B, at 100-600 seconds is presented a signal obtained from 10 mM pyruvate in PBS, and at 800-1500 seconds is presented a signal obtained from PBS only.

Example 4

Calibration

For measuring (e.g., monitoring) an amount (level, concentration) of a bioanalyte in vivo, a self-calibration method was developed, since it is impossible to build a calibration curve for the sensing system inside a living organism. In this method, a sensing system comprising an array of SiNWs is utilized, wherein some of the nanowires are as described in Example 2 hereinabove, and some of the nanowires have attached thereto a hydrogel impregnating a non-sensing moiety, that is, a moiety that is not analyte-specific, and which does not interact with a bioanalyte. Such a moiety can be, for example, a protein such as bovine serum albumin. Alternatively, some of the nanowires have attached thereto a non-impregnated hydrogel. Because there is no specific deformation of the hydrogel impregnating such a non-sensing moiety, a signal detected from such nanowires represents a background of a physiological environment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A sensing system for determining and/or monitoring a presence and/or level of an analyte in a sample, wherein the sample is a biological sample and wherein the analyte is a bioanalyte, the system comprising a field effect transistor having a source electrode, a drain electrode, a gate electrode, and a channel between said source and drain electrodes, said channel being a semiconducting nanostructure having a hydrogel covalently attached thereto, said hydrogel having incorporated therein a sensing moiety which is a bioanalyte-specific reagent and being configured such that upon contacting the bioanalyte, said nanostructure exhibits a detectable change in an electrical property, said electrical property comprising electron density on a surface of said nanostructure, wherein upon contacting the analyte, said hydrogel exhibits a deformation, said deformation leading to said detectable change in said electrical property of said nanostructure, wherein said nanostructure is a silicon nanowire, and wherein said hydrogel is selected capable of impregnating a biological moiety while maintaining an activity of said biological moiety.

2. The sensing system of claim 1, wherein the bioanalyte is a metabolite.

3. The sensing system of claim 2, wherein said sensing moiety is a redox enzyme specific to said metabolite.

4. The sensing system of claim 1, wherein the bioanalyte is a biomarker protein.

5. The system of claim 4, wherein the bioanalyte is an antigen and said sensing moiety is an antibody specific to said antigen.

6. The sensing system of claim 1, wherein said hydrogel is covalently attached to said nanostructure via a linking moiety.

7. The sensing system of claim 1, wherein said deformation comprises a change in a volume of said hydrogel.

8. The sensing system of claim 1, wherein said deformation comprises a change in spatial distribution of molecules and/or charge in the hydrogel.

9. The sensing system of claim 1, comprising a plurality of said nanostructures.

10. The sensing system of claim 9, wherein said hydrogel is covalently attached to at least two of said nanostructures.

11. The sensing system of claim 9, wherein in at least one portion of said nanostructures said hydrogel has a first sensing moiety incorporated therein and/or thereon and in at least another portion of said nanostructures said hydrogel has a second sensing moiety incorporated therein and/or thereon, said first and second sensing moieties being different from one another.

12. The sensing system of claim 9, further comprising at least one nanostructure having a hydrogel covalently attached thereto, said hydrogel has a non-sensing moiety incorporated therein and/or thereon.

13. The sensing system of claim 1, wherein said hydrogel is in a form of a nanoparticle or in a form of a film.

14. The sensing system of claim 1, being in a form of a skin patch.

15. A system comprising a sensing compartment comprising the sensing system of claim 1, and at least one additional compartment being in communication with the sensing compartment.

16. The system of claim 15, wherein said at least one additional compartment is configured to contain at least a portion of said sample.

17. The system of claim 15, wherein said at least one additional compartment is configured to contain a therapeutically active agent.

18. The system of claim 17, wherein said additional compartment is configured to controllably release said therapeutically active agent.

19. The system of claim 18, wherein said additional compartment is configured to controllably release said therapeutically active agent responsively to said detectable change in electrical property of said nanostructure.

20. The system of claim 15, wherein said at least one additional compartment comprises an additional sensing system.

21. The system of claim 15, being in a form of a skin patch.

22. A method of determining or monitoring a presence and/or a level of at least one bioanalyte in a biological sample, the method comprising contacting at least a portion of the biological sample with the sensing system of claim 1, wherein said detectable change in said electrical property is indicative of the presence and/or level of the bioanalyte in the sample.

23. The method of claim 22, being for diagnosing and/or monitoring a disease associated with said bioanalyte in a subject.

24. A method of determining or monitoring a presence and/or a level of at least one bioanalyte in a biological sample, the method comprising contacting at least a portion of the biological sample with the system of claim 15, wherein said detectable change in said electrical property is indicative of the presence and/or level of the bioanalyte in the sample.

25. The method of claim 24, being for diagnosing and/or monitoring a disease associated with said bioanalyte in a subject.

26. The method of claim 25, wherein said system further comprises a compartment configured for releasing a therapeutically active agent, the method being for determining and/or monitoring an efficacy of said therapeutic agent towards said disease in said subject and/or for treating said disease.

* * * * *